US008951265B2

(12) United States Patent
Schwappach

(10) Patent No.: US 8,951,265 B2
(45) Date of Patent: Feb. 10, 2015

(54) FIXATION SYSTEM FOR ORTHOPEDIC DEVICES

(71) Applicant: RDC Holdings, LLC, North Oaks, MN (US)

(72) Inventor: Karl G. Schwappach, North Oaks, MN (US)

(73) Assignee: RDC Holdings, LLC, North Oaks, MN (US)

( * ) Notice: Subject to any disclaimer, the term of this patent is extended or adjusted under 35 U.S.C. 154(b) by 235 days.

(21) Appl. No.: 13/658,182

(22) Filed: Oct. 23, 2012

(65) Prior Publication Data

US 2013/0046351 A1    Feb. 21, 2013

Related U.S. Application Data

(63) Continuation-in-part of application No. PCT/US2012/043346, filed on Jun. 20, 2012.

(60) Provisional application No. 61/498,687, filed on Jun. 20, 2011, provisional application No. 61/515,009, filed on Aug. 4, 2011, provisional application No. 61/591,304, filed on Jan. 27, 2012.

(51) Int. Cl.
*A61B 17/58*    (2006.01)
*A61B 17/60*    (2006.01)
(Continued)

(52) U.S. Cl.
CPC ....... *A61F 2/0811* (2013.01); *A61F 2002/0841* (2013.01); *A61F 2002/087* (2013.01)
USPC ............. 606/105; 606/92; 606/327; 606/304; 606/264; 606/310

(58) Field of Classification Search
USPC ............. 606/105, 92–95, 323, 326, 327, 304, 606/264, 310
See application file for complete search history.

(56) References Cited

U.S. PATENT DOCUMENTS

| 806,406 A | 12/1905 | Farrington |
| 3,779,239 A | 12/1973 | Fischer et al. |

(Continued)

FOREIGN PATENT DOCUMENTS

| WO | WO 93/00432 A1 | 1/1993 |
| WO | WO 94/02693 A1 | 2/1994 |

(Continued)

OTHER PUBLICATIONS

ASTM standard F543-02, Standard Specification and Test Methods for Metallic Medical Bone Screws, Annex A3—Test Method for Determining the Axial Pullout Strength of Medical Bone Screws (abstract).

(Continued)

*Primary Examiner* — Andrew Yang
*Assistant Examiner* — Olivia C Chang

(57) ABSTRACT

A fixation system configured to releasably secure an orthopedic implant to a bone. The fixation system including at least one expandable member that is inserted through the lumen and positioned in cancellous bone near the distal portion of the orthopedic implant. A delivery tube delivers a flowable biomaterial to the expandable member. The expand fixation structure includes at least one dimension greater than a corresponding dimension on the orthopedic implant to secure the orthopedic implant in the bone. An insert is secured in the lumen to releasably attach the fixation system to the orthopedic implant. The expandable member is detachable from the orthopedic implant to facilitate subsequent removal of the orthopedic implant from the bone.

19 Claims, 24 Drawing Sheets

(51) Int. Cl.
*A61F 2/00* (2006.01)
*A61F 2/08* (2006.01)

(56) References Cited

U.S. PATENT DOCUMENTS

| | | | |
|---|---|---|---|
| 3,983,736 A | 10/1976 | King, Jr. | |
| 4,536,115 A | 8/1985 | Helderman | |
| 4,669,473 A | 6/1987 | Richards et al. | |
| 4,877,864 A | 10/1989 | Wang et al. | |
| 5,013,649 A | 5/1991 | Wang et al. | |
| 5,053,035 A | 10/1991 | McLaren | |
| 5,084,050 A | 1/1992 | Draenert | |
| 5,106,748 A | 4/1992 | Wozney et al. | |
| 5,108,932 A | 4/1992 | Wolfbeis | |
| 5,116,738 A | 5/1992 | Wang et al. | |
| 5,187,076 A | 2/1993 | Wozney et al. | |
| 5,312,214 A | 5/1994 | Morton | |
| 5,356,413 A | 10/1994 | Martins et al. | |
| 5,366,875 A | 11/1994 | Wozney et al. | |
| 5,372,599 A | 12/1994 | Martins | |
| 5,505,735 A | 4/1996 | Li | |
| 5,514,137 A | 5/1996 | Coutts | |
| 5,549,679 A | 8/1996 | Kuslich | |
| 5,549,701 A | 8/1996 | Mikhail | |
| 5,554,171 A | 9/1996 | Gatturna et al. | |
| 5,571,104 A | 11/1996 | Li | |
| 5,647,874 A | 7/1997 | Hayhurst | |
| 5,649,963 A | 7/1997 | McDevitt | |
| 5,662,654 A | 9/1997 | Thompson | |
| 5,681,872 A | 10/1997 | Erbe | |
| 5,693,011 A | 12/1997 | Onik | |
| 5,702,397 A | 12/1997 | Goble et al. | |
| 5,720,753 A | 2/1998 | Sander et al. | |
| 5,725,557 A | 3/1998 | Gatturna et al. | |
| 5,914,356 A | 6/1999 | Erbe | |
| 5,928,239 A | 7/1999 | Mirza | |
| 5,972,015 A | 10/1999 | Scribner et al. | |
| 5,984,927 A | 11/1999 | Wenstrom, Jr. et al. | |
| 5,990,194 A | 11/1999 | Dunn et al. | |
| 6,042,583 A | 3/2000 | Thompson et al. | |
| 6,113,611 A | 9/2000 | Allen et al. | |
| 6,146,406 A | 11/2000 | Shluzas et al. | |
| 6,200,330 B1 | 3/2001 | Benderev et al. | |
| 6,203,572 B1 | 3/2001 | Johnson et al. | |
| 6,210,413 B1 | 4/2001 | Justis et al. | |
| 6,228,123 B1 | 5/2001 | Dezzani | |
| 6,235,043 B1 | 5/2001 | Reiley et al. | |
| 6,276,883 B1 | 8/2001 | Unsworth et al. | |
| 6,299,448 B1 | 10/2001 | Zdrahala et al. | |
| 6,387,041 B1 | 5/2002 | Harari et al. | |
| 6,440,135 B2 | 8/2002 | Orbay et al. | |
| 6,447,524 B1 | 9/2002 | Knodel et al. | |
| 6,451,024 B1 | 9/2002 | Thompson et al. | |
| 6,494,657 B2 | 12/2002 | Unsworth et al. | |
| 6,506,194 B1 | 1/2003 | Hajianpour | |
| 6,517,542 B1 | 2/2003 | Papay et al. | |
| 6,551,321 B1 | 4/2003 | Burkinshaw et al. | |
| 6,620,162 B2 | 9/2003 | Kuslich et al. | |
| 6,656,184 B1 | 12/2003 | White et al. | |
| 6,770,676 B2 | 8/2004 | Foerster | |
| 6,770,695 B2 | 8/2004 | Ricci et al. | |
| 6,783,530 B1 | 8/2004 | Levy | |
| 6,835,206 B2 | 12/2004 | Jackson | |
| 6,860,691 B2 | 3/2005 | Unsworth et al. | |
| 7,090,690 B2 | 8/2006 | Foerster et al. | |
| 7,172,615 B2 | 2/2007 | Morriss et al. | |
| 7,172,629 B2 | 2/2007 | McKay | |
| 7,226,481 B2 | 6/2007 | Kuslich | |
| 7,377,934 B2 | 5/2008 | Lin et al. | |
| 7,488,320 B2 | 2/2009 | Middleton | |
| 7,544,196 B2 | 6/2009 | Bagga et al. | |
| 7,589,133 B2 | 9/2009 | Pomrink | |
| 7,632,277 B2 | 12/2009 | Woll et al. | |
| 7,671,014 B2 | 3/2010 | Beals et al. | |
| 7,717,947 B1 | 5/2010 | Wilberg et al. | |
| 7,789,901 B2 | 9/2010 | Froehlich | |
| 7,846,162 B2 | 12/2010 | Nelson et al. | |
| 7,862,612 B2 | 1/2011 | Re et al. | |
| 7,967,861 B2 | 6/2011 | Montgomery et al. | |
| 8,003,133 B2 | 8/2011 | Li et al. | |
| 8,048,158 B2 | 11/2011 | Hays et al. | |
| 8,128,632 B2 | 3/2012 | Paris et al. | |
| 8,192,835 B2 | 6/2012 | Chi | |
| 8,231,632 B1 | 7/2012 | Jordan et al. | |
| 8,241,340 B2 | 8/2012 | Froehlich | |
| 2002/0032444 A1 | 3/2002 | Mische | |
| 2002/0082694 A1 | 6/2002 | McKay | |
| 2003/0114933 A1 | 6/2003 | Bouttens et al. | |
| 2004/0024456 A1 | 2/2004 | Brown, Jr. et al. | |
| 2004/0181225 A1 | 9/2004 | Songer | |
| 2004/0225361 A1 | 11/2004 | Glenn et al. | |
| 2006/0100623 A1 | 5/2006 | Pennig | |
| 2006/0100630 A1 | 5/2006 | West, Jr. | |
| 2006/0149280 A1 | 7/2006 | Harvie et al. | |
| 2006/0200142 A1 | 9/2006 | Sohngen et al. | |
| 2006/0204586 A1 | 9/2006 | Alexander et al. | |
| 2006/0271192 A1 | 11/2006 | Olsen et al. | |
| 2007/0203498 A1 | 8/2007 | Gerber et al. | |
| 2008/0015710 A1 | 1/2008 | Hays et al. | |
| 2008/0090936 A1 | 4/2008 | Fujimura et al. | |
| 2008/0255560 A1 | 10/2008 | Myers et al. | |
| 2008/0269743 A1 | 10/2008 | McNamara et al. | |
| 2009/0018542 A1 | 1/2009 | Saravia et al. | |
| 2009/0024147 A1 | 1/2009 | Ralph et al. | |
| 2009/0208907 A1 | 8/2009 | Dosta et al. | |
| 2009/0281580 A1 | 11/2009 | Emannuel | |
| 2010/0087821 A1 | 4/2010 | Trip et al. | |
| 2010/0094292 A1 | 4/2010 | Parrott | |
| 2010/0179591 A1 | 7/2010 | Saltzman et al. | |
| 2010/0255042 A1 | 10/2010 | Jennissen et al. | |
| 2010/0268227 A1 | 10/2010 | Tong et al. | |
| 2010/0286692 A1 | 11/2010 | Greenhalgh et al. | |
| 2010/0298937 A1 | 11/2010 | Laurencin et al. | |
| 2010/0312275 A1 | 12/2010 | Euteneuer et al. | |
| 2010/0331898 A1 | 12/2010 | Froehlich | |
| 2010/0331983 A1 | 12/2010 | Sankaran | |
| 2011/0046630 A1 | 2/2011 | Murphy | |
| 2011/0082564 A1 | 4/2011 | Liu et al. | |
| 2011/0087296 A1 | 4/2011 | Reiley et al. | |
| 2011/0125158 A1* | 5/2011 | Diwan et al. | 606/93 |
| 2011/0184516 A1 | 7/2011 | Baird et al. | |
| 2012/0095463 A1 | 4/2012 | Rains et al. | |
| 2012/0107401 A1 | 5/2012 | McKay | |
| 2012/0195982 A1 | 8/2012 | Hu et al. | |
| 2012/0225972 A1 | 9/2012 | Ameer et al. | |
| 2013/0144348 A1 | 6/2013 | Schwappach et al. | |

FOREIGN PATENT DOCUMENTS

| | | |
|---|---|---|
| WO | WO 94/26892 A1 | 11/1994 |
| WO | WO 01/08602 A1 | 2/2001 |
| WO | WO 2005/112804 A1 | 12/2005 |
| WO | WO 2011/044697 A1 | 4/2011 |
| WO | WO 2012/177759 A1 | 12/2012 |

OTHER PUBLICATIONS

B.E. McKoy and Y.H., An Expandable Anchor for Fixation in Osteoporotic Bone, An Journal of Orthopaedic Research, Jan. 2001, 19:545-547 (abstract).

B.E. McKoy, 47th Annual Meeting, Orthopaedic Research Society, Feb. 25-28, 2001, Session 19, Bone Mechanics II (abstract).

H.C.M. Amstutz et al., Mechanism and Clinical Significance of Wear Debris-Induced Osteolysis, Clin. Orthop., Mar. 1992, 276:7-18 (abstract).

J.G. Heller et al., Biomechanical Study of Screws in the Lateral Masses: Variables Affecting Pull-out Resistance, J Bone Joint Surg. [AM], Sep. 1996, 78:1315-1321 (abstract).

O.R. Zindrick et al., A Biomechanical Study of Intrapeduncular Screw Fixation in the Lumbosacral Spine, Clinical Orthopaedics, Feb. 1986, 203:99-112. (abstract).

(56) References Cited

OTHER PUBLICATIONS

T.C. Ryken et al., Biomedical Analysis of Bone Mineral Density, Insertion Technique, Screw Torque, and Holding Strength of Anterior Cervical Plate Screws, Journal of Neurosurgergy, Aug. 1995, 83:325-329 (abstract).

PCT/US2012/43346, International Search Report dated Oct. 12, 2012, 1 page.

Application and File history for U.S. Appl. No. 13/743,869, filed Jan. 17, 2013. Inventors: Schwappach et al.

PCT/US2012/043346, International Preliminary Report on Patentability, dated Dec. 23, 2013, 8 pages.

* cited by examiner

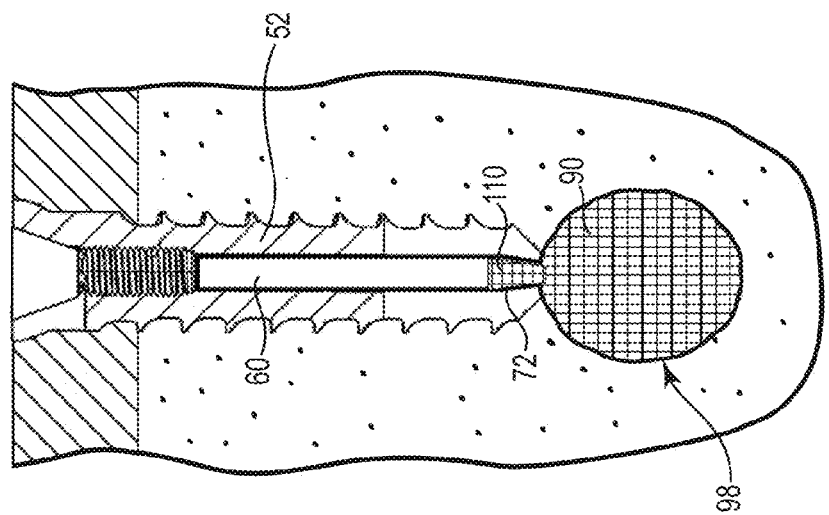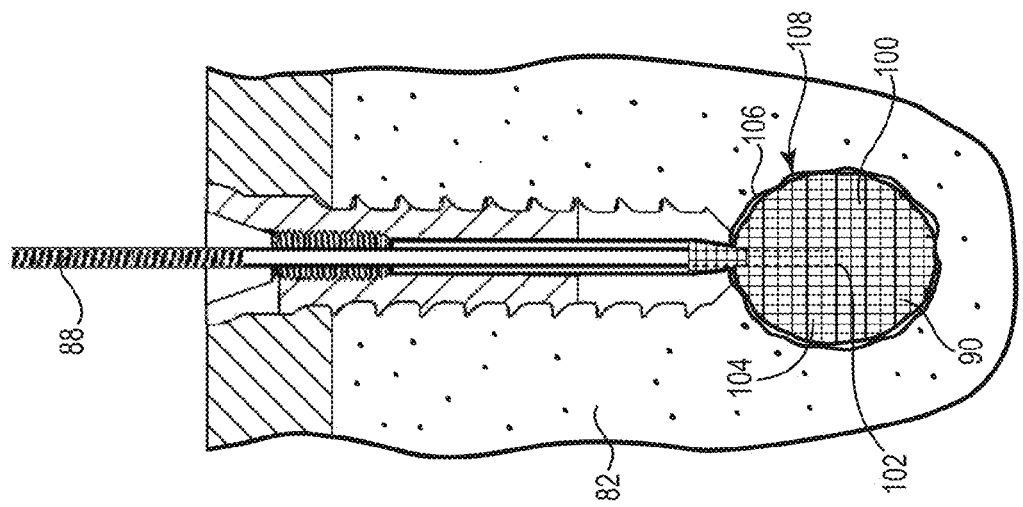

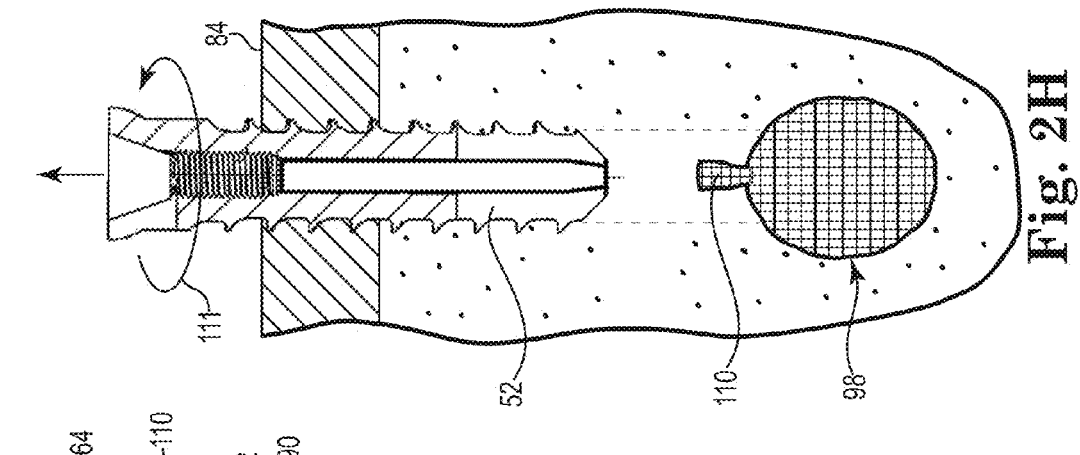
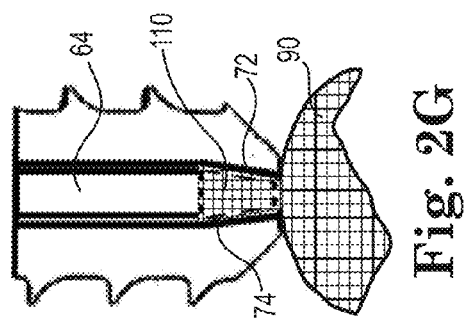
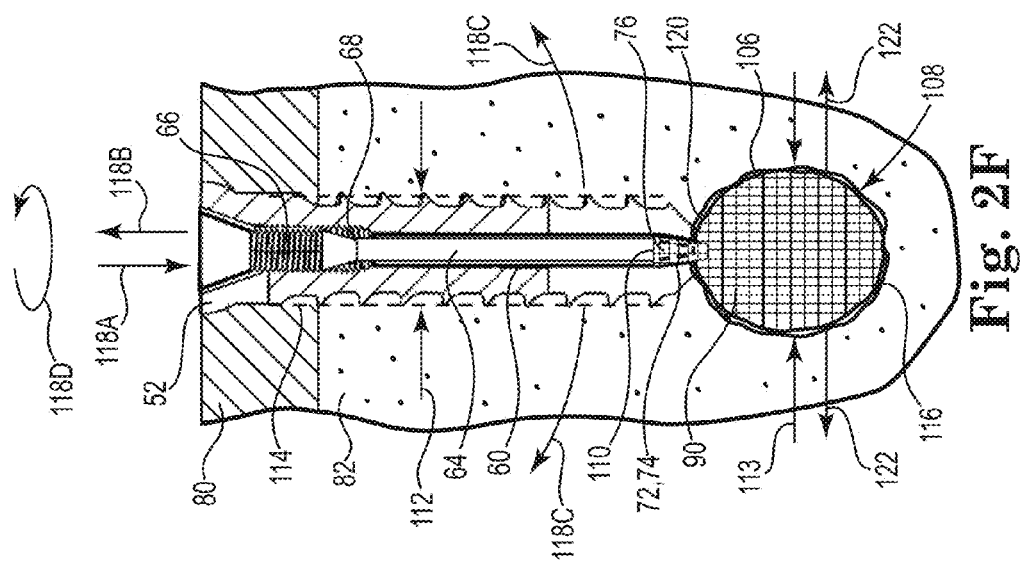

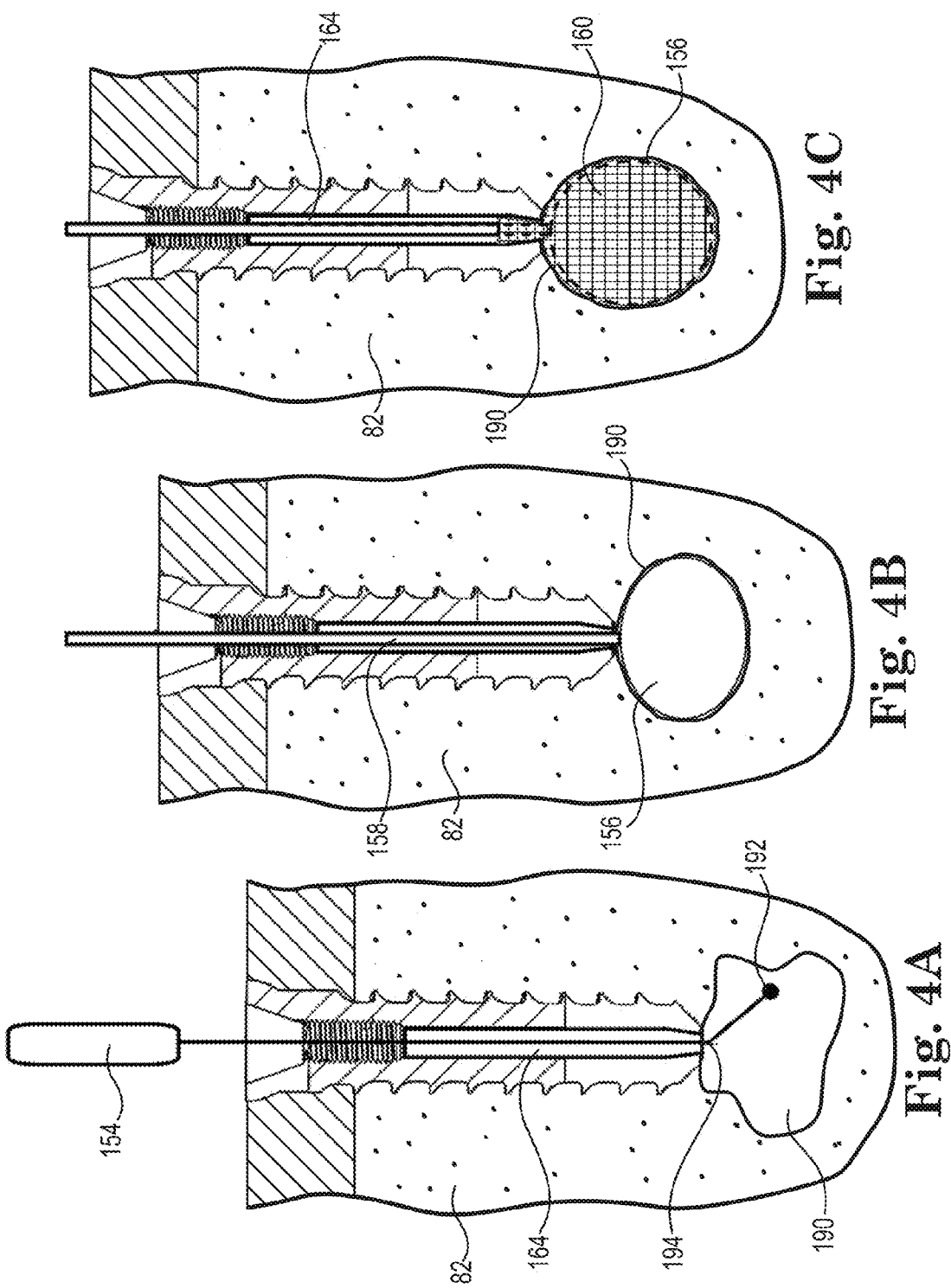

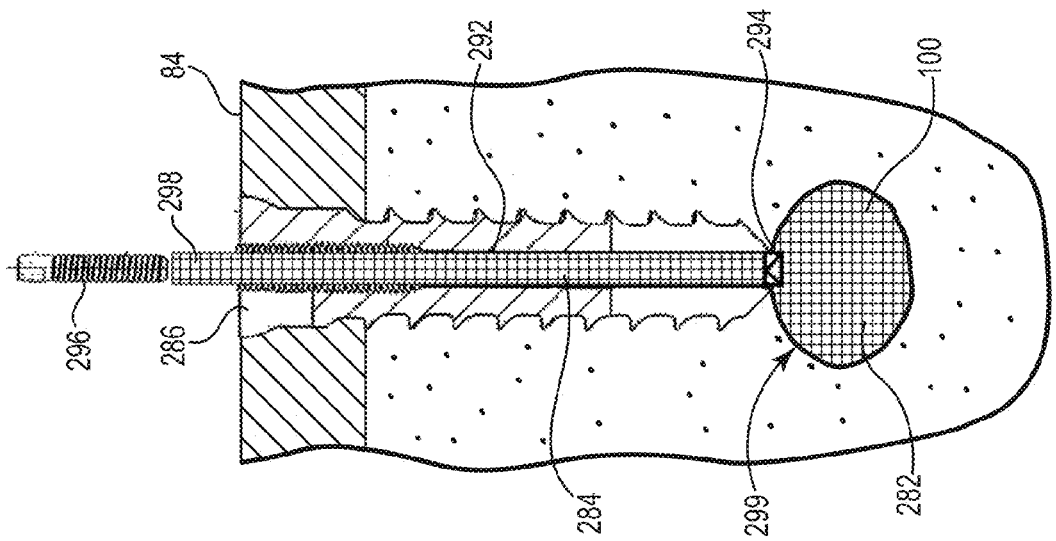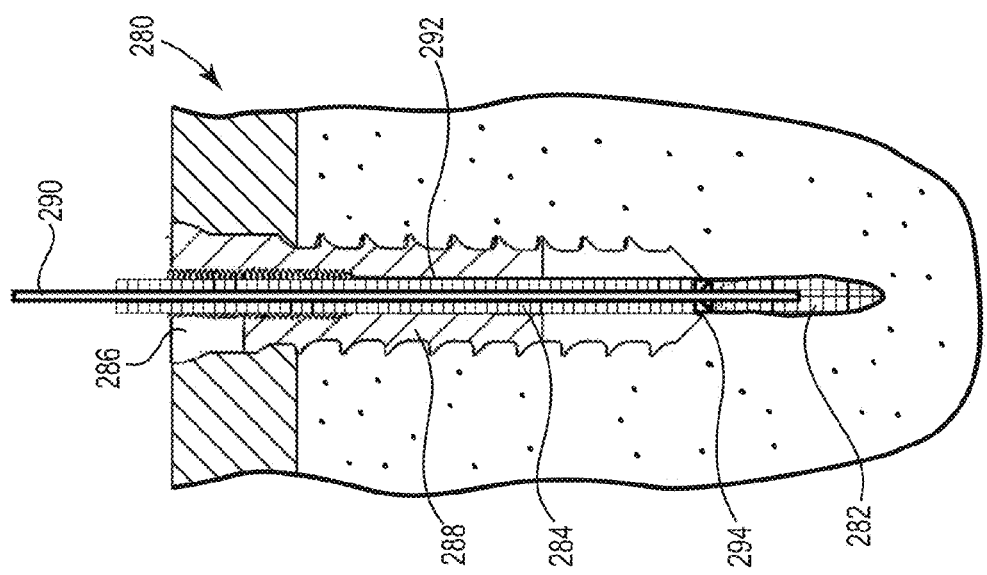

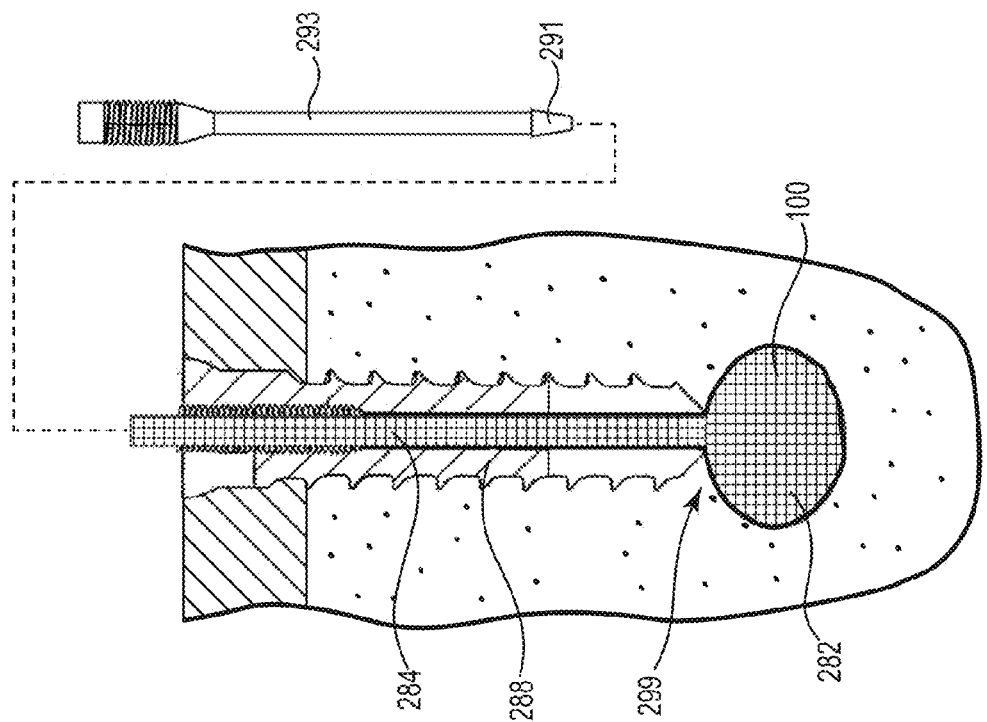
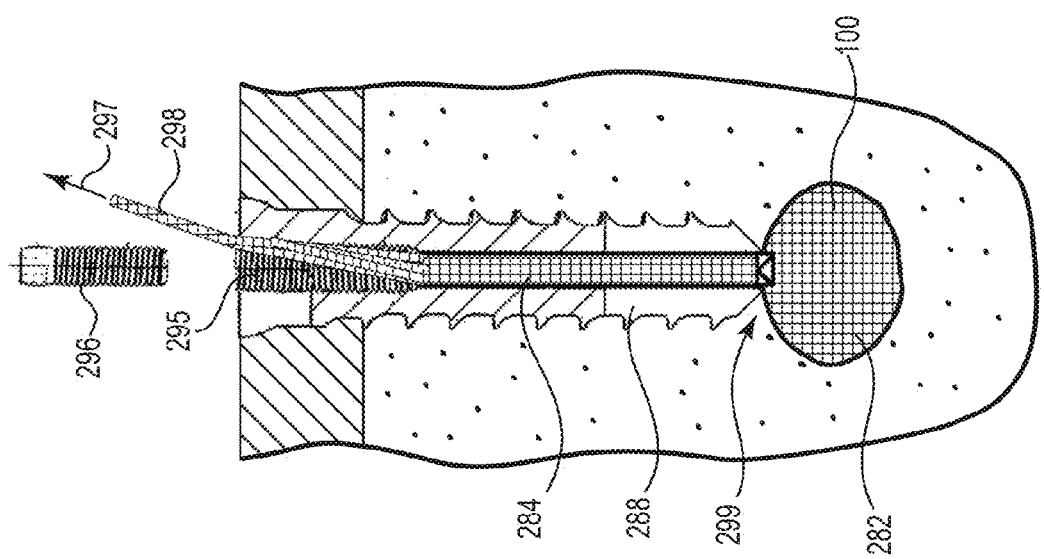
Fig. 8D
Fig. 8C

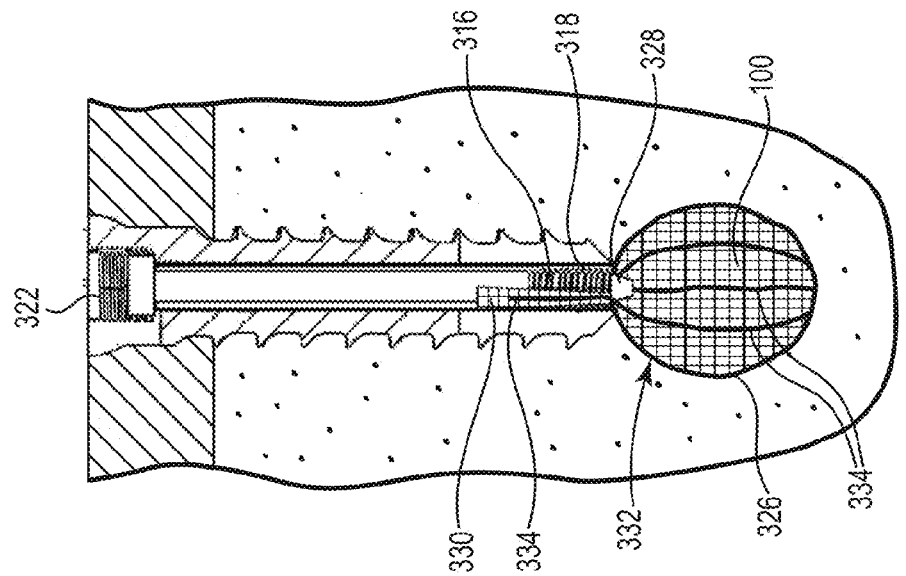
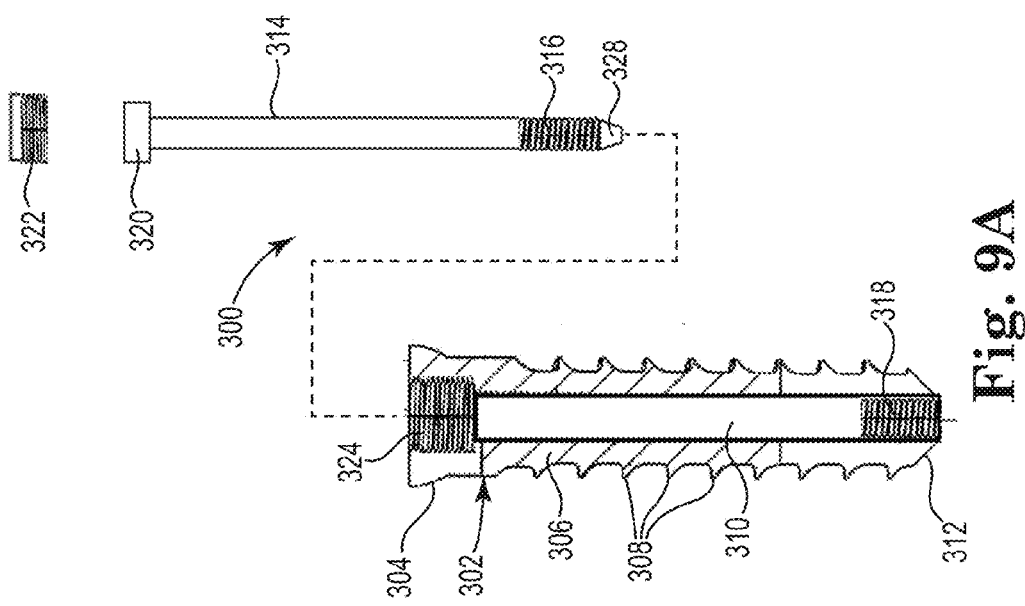

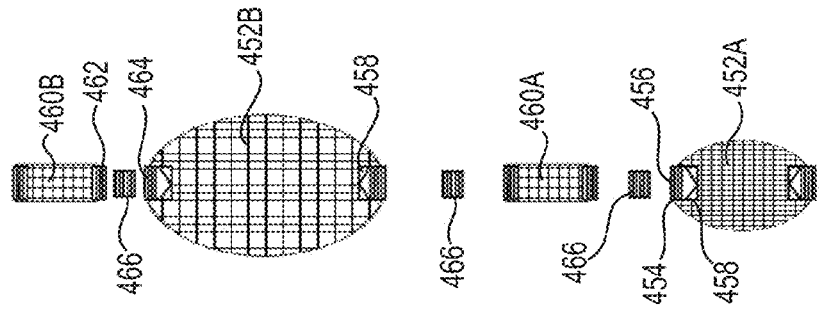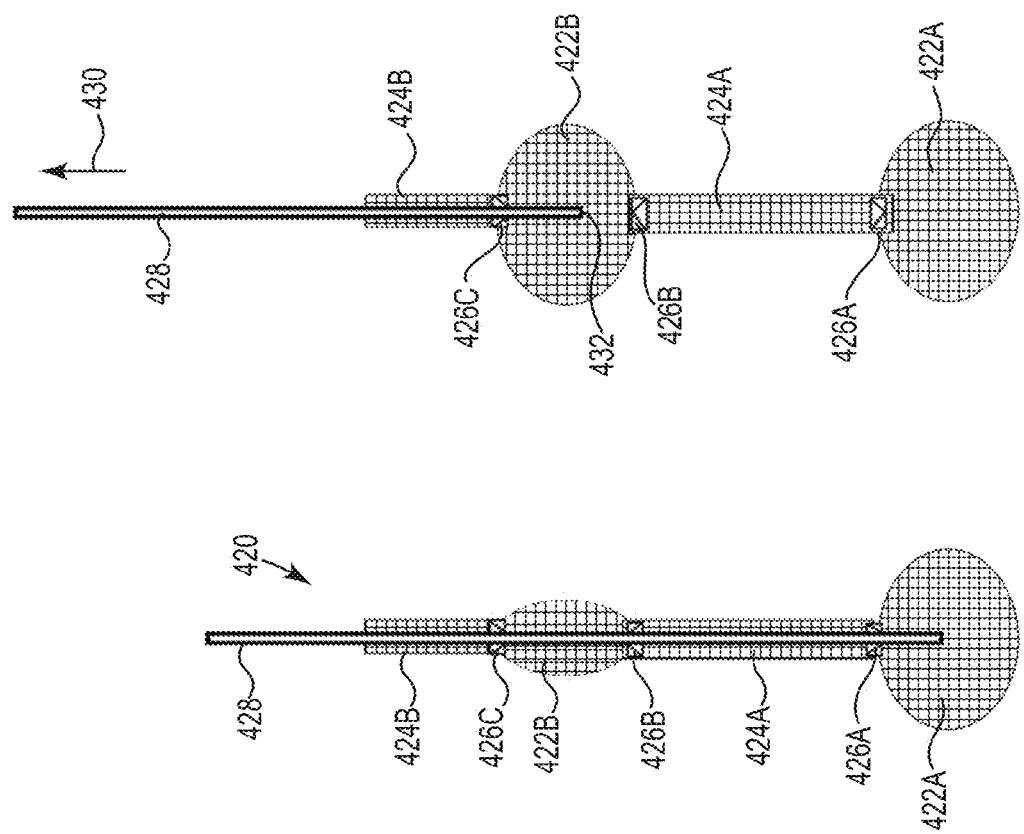

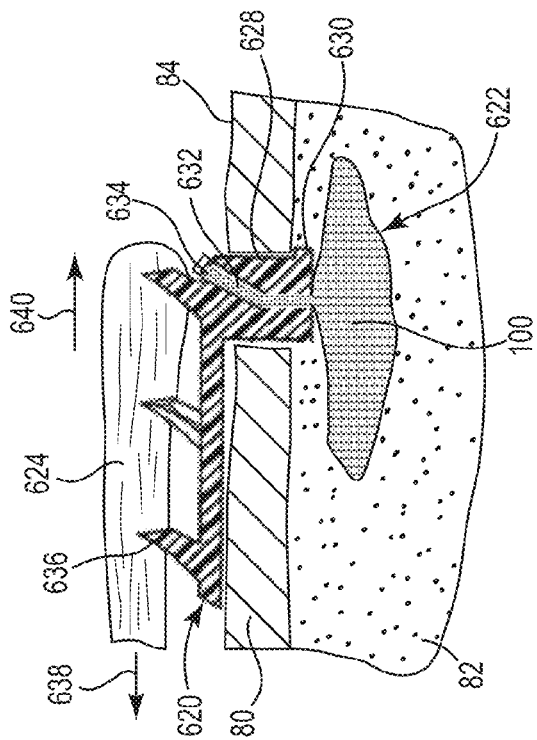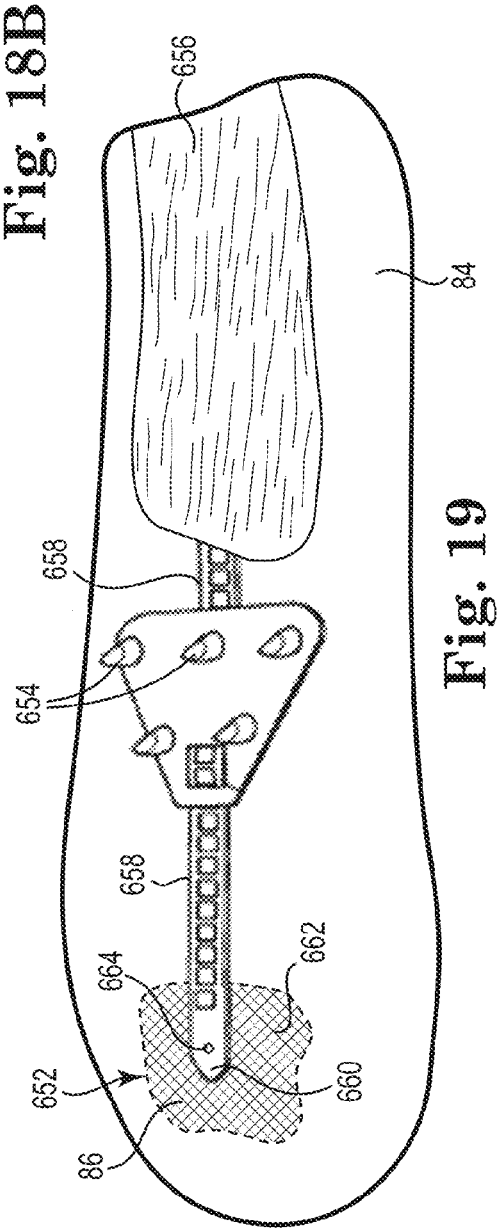

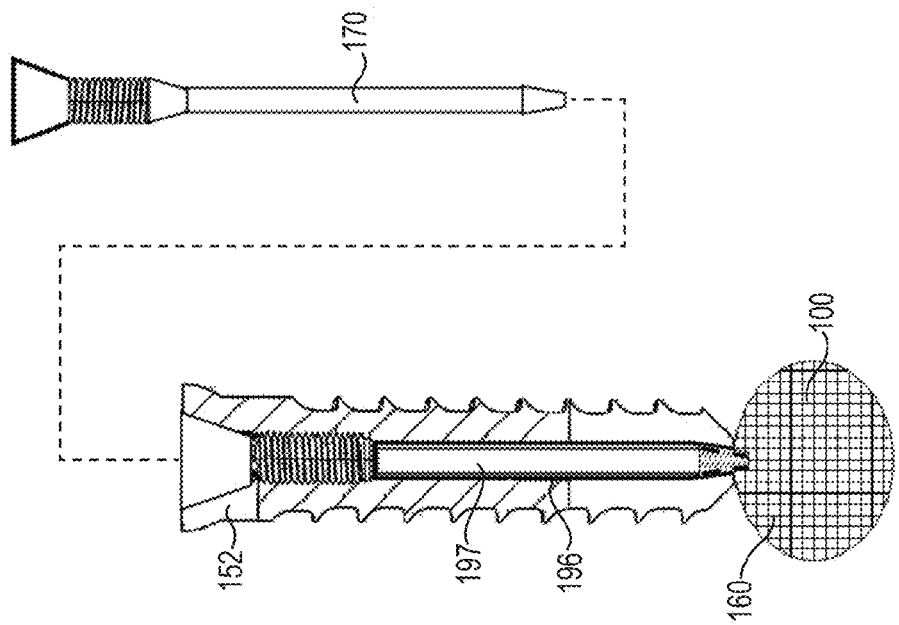
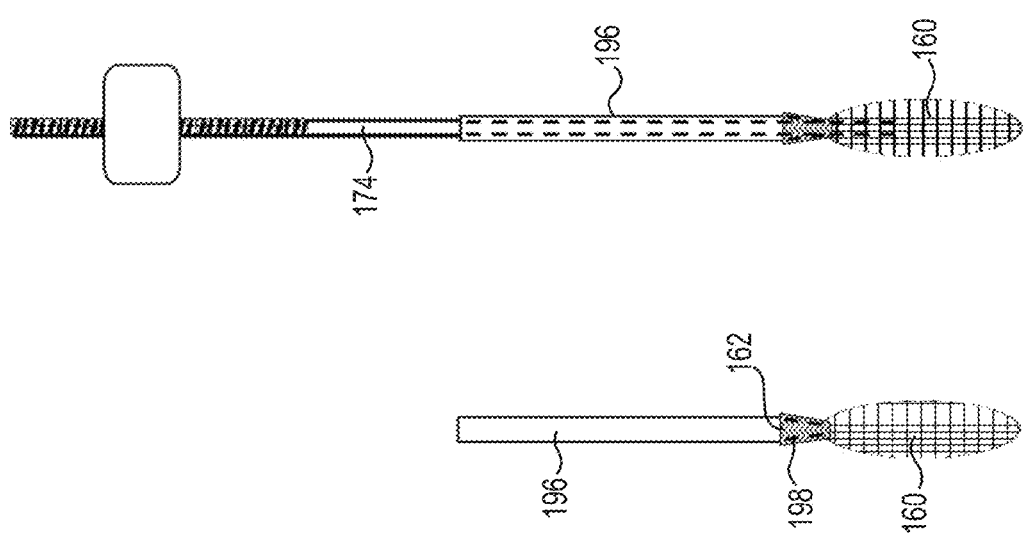
Fig. 20A   Fig. 20B   Fig. 20C

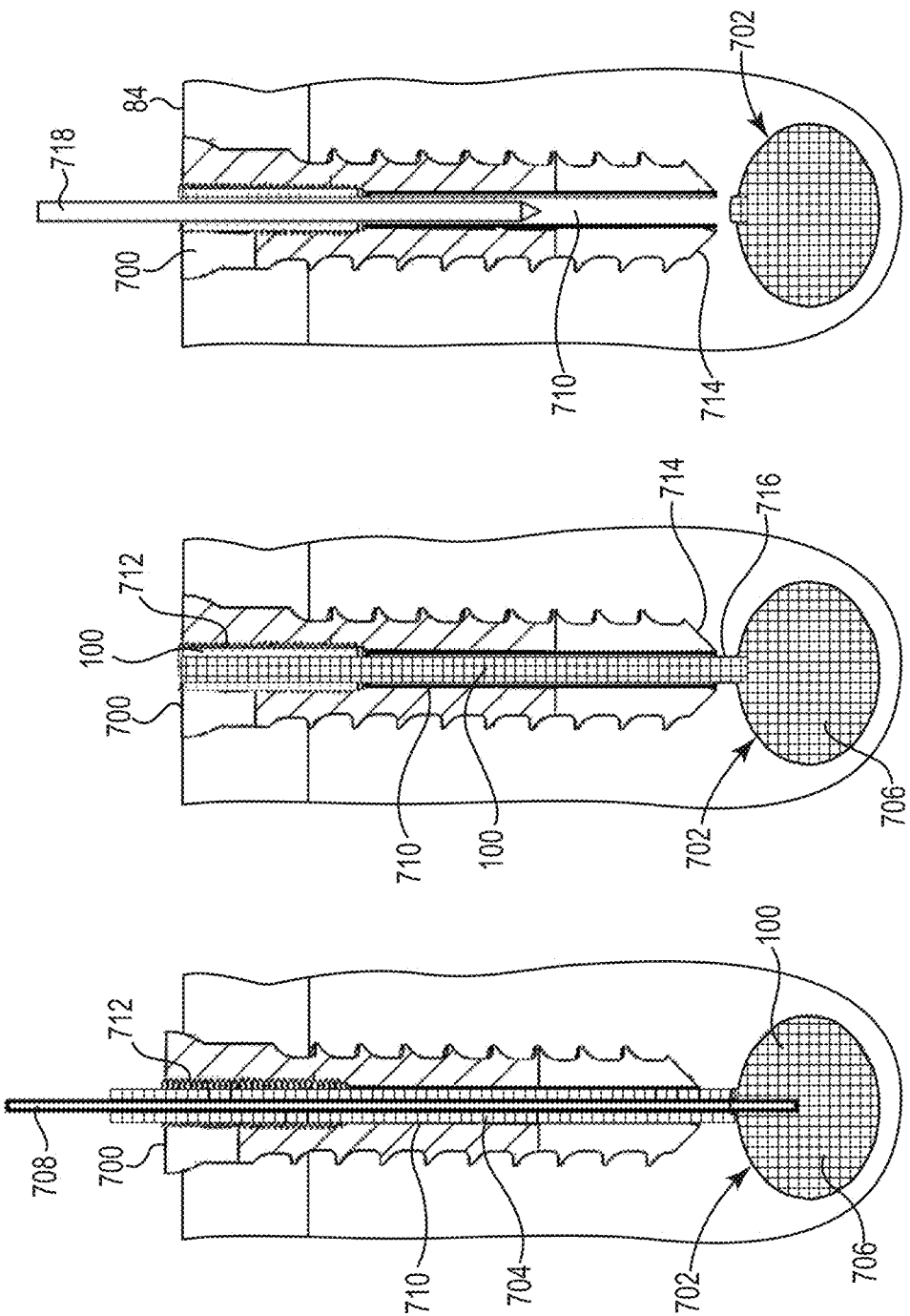

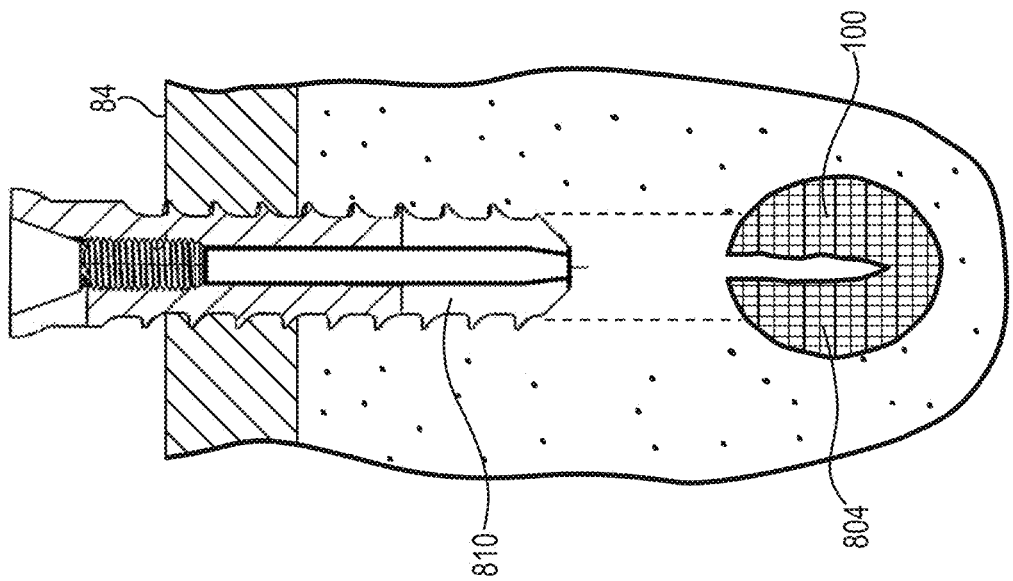
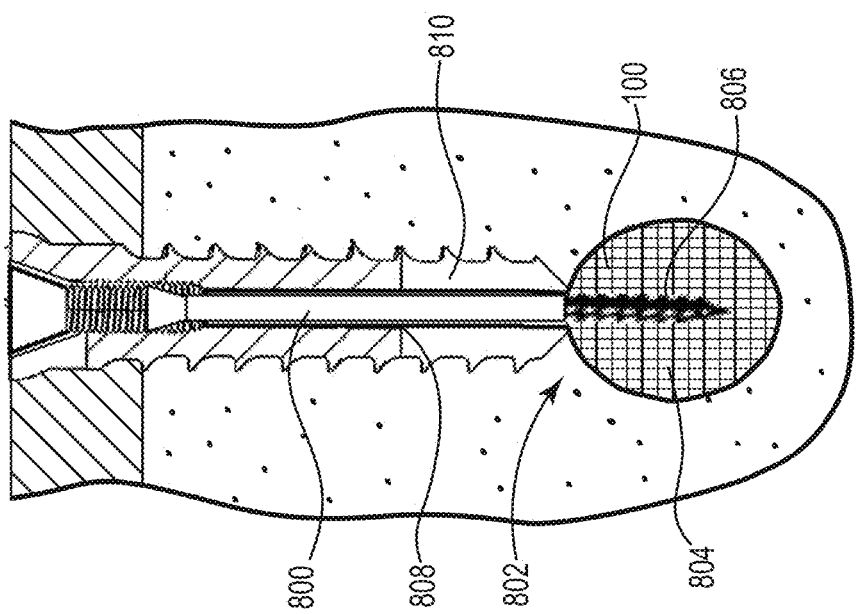

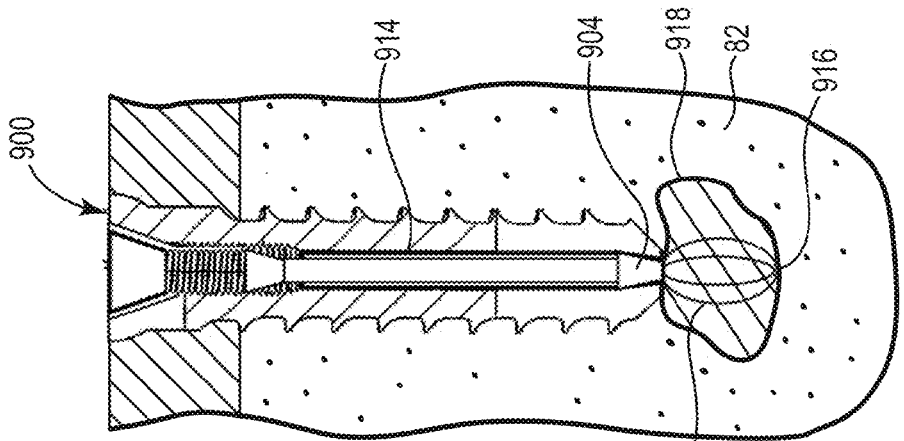
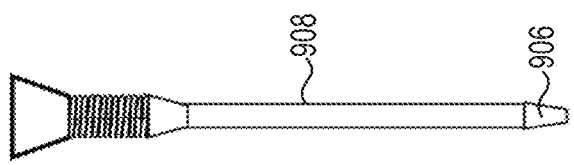
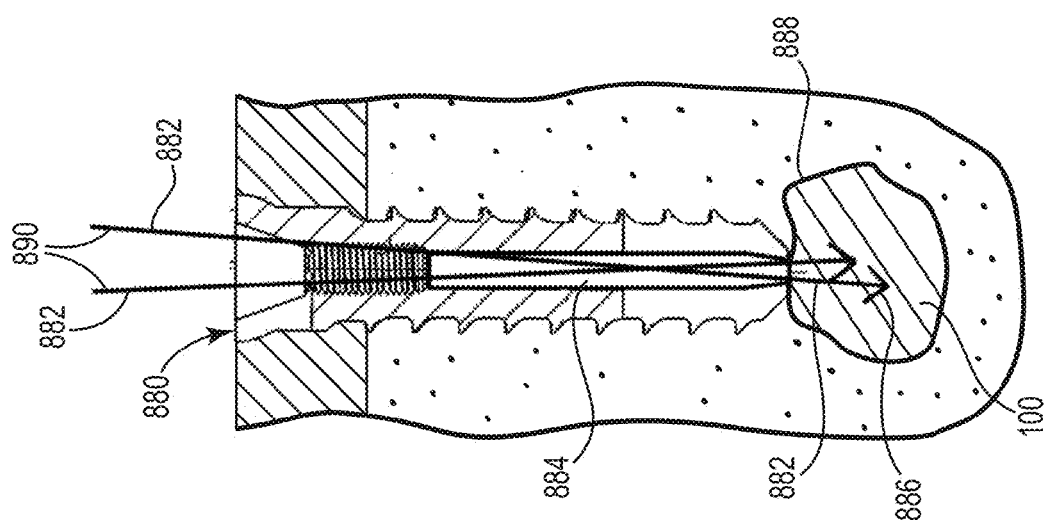

FIXATION SYSTEM FOR ORTHOPEDIC DEVICES

RELATED APPLICATIONS

The present application is a continuation-in-part of PCT application PCT/US12/43346, entitled System and Method for Repairing Joints filed Jun. 20, 2012, which claims the benefit of U.S. Provisional Application No. 61/498,687, entitled Orthopedic Fixation System and Method of Use, filed Jun. 20, 2011; U.S. Provisional Application No. 61/515,009, entitled Orthopedic Fixation System and Method of Use, filed Aug. 4, 2011; and U.S. Provisional Application No. 61/591,304, entitled Fixation System and Method for Repairing Joints, filed Jan. 27, 2012, the disclosures of which are hereby incorporated by reference.

FIELD OF THE INVENTION

The present disclosure is directed to a fixation system used to supplement the fixation of an orthopedic implant. The fixation system includes a fixation structure that is releasably secured to the orthopedic implant and embedded in cancellous bone by a biomaterial. The biomaterial is preferably a resorbable, bone-growth stimulating composition that interacts with the cancellous bone to incorporate the fixation structure in the cancellous bone.

BACKGROUND OF THE INVENTION

A wide variety of implantable orthopedic implants and procedures are known for stabilizing and securing fractures in bones, replacing damaged joints, attaching tissue to bone, and the like. For example, fixation plates and intramedullary devices can be surgically positioned to span the fracture site. Intramedullary devices are also commonly used to attach replacement joints to long bones. A variety of orthopedic fasteners, such as screws, pins, and the like, are typically used to help secure these orthopedic implants to the bone.

The ability of orthopedic fasteners to resist loosening is related to bone quality (O. R. Zindric et al Clinical Orthopaedics (1986) 203:99-112), while the holding power of an orthopedic fastener correlates with mineral density (T. C. Ryken et al Journal of Neurosurgery (1995) 83:325-329). If the bone at the implantation site is compromised, either before, such as due to osteoporosis, or as a result of the implantation procedure, the surgeon may have limited options for securing the orthopedic implant.

Loosening and backing out of an orthopedic fasteners can result in decreased structural integrity of the bone. Once an orthopedic fastener manages to work itself loose, wear and tear to the opening or space in the bone within which it was received may prohibit securely refastening the orthopedic fastener in the bone. Adding more orthopedic fasteners to compensate for the compromised bone complicates future revision or removal, and may further weaken the bone. For example, the formation of screw holes in the cortical bone provides stress risers that substantially increases the risk of bone re-fracture. Since orthopedic implants interfere with revascularization in the bone it is preferred to minimize the number of such devices.

U.S. Pat. Nos. 7,789,901 and 8,241,340 (Froehlich) discloses an expandable structure fixedly attached to a distal end of a bone anchor. The expandable structure is configured to expand when a filler material is delivered through a fill port and into the expandable structure. The distal end of the bone anchor is embedded in the cured filler material to form a permanent connection with the bone.

U.S. Pat. No. 7,717,947 (Wilberg et al.) discloses a cannulated bone screw with an axial bore and exit ports near the threads. Bone cement is injected through the axial bore and flows out the exit ports to permanently anchor the bone screw in the bone. The bone cement is located at the interface of the bone screw to the bone.

U.S. Pat. No. 7,488,320 (Middleton) discloses an anchor for an orthopedic implant similar to Wilberg with lumens for injecting bone cement. The bone cement forms an interlocking relationship with structures and voids on a preformed element to permanently anchor the device in the bone. Once the injectable material is hardened, the anchors of Wilberg is permanently locked in position.

The strategies noted above rely on bone cement to augment pull out strength. PMMA is exothermic upon polymerization and toxic monomers can cause bone necrosis, proliferation of fibrous tissue layers and other adverse biological responses (H. C. M. Amstutz et al Clin. Orthop. (1992) 276:7-18 and J. G. Heller et al J. Bone J. Surg. [Am] (1996) 78:1315-1321). Cement induced osteolysis or necrotic bone may impair the fixation and lead to eventual fastener loosening and failure. In the case of failure it is often difficult to remove cement from the bone and it is usually associated with excessive damage to the surrounding bone.

In some cases an orthopedic implant may need to be adjusted or corrected after the original implantation surgery is completed. Such revisions may be necessitated by re-fracture, infection, deterioration of the bone, situations where the patient's subsequent growth requires revision of the implant so as not to impede proper growth, and the need to move corrective forces of the orthopedic implant on an area or in an orientation that is different from what was originally needed. In those cases, an adjustment, correction or other revision of the implanted orthopedic implant will require unlocking and removal of the orthopedic fasteners. Bone cement at the interface with the orthopedic fasteners greatly complicates this procedure.

A number of cementless solutions have been proposed, such as interlocking screws (B. E. McKoy, 47.sup.th Annual Meeting, Orthopaedic Research Society, Feb. 25-28, 2001, Session 19, Bone Mechanics II) and bone screw anchors (B. E. McKoy and Y. H. An Journal of Orthopaedic Research (2001) 19:545-547). Other bone implantation/fixation devices and methods are known in the art, for example, U.S. 2004/0181225, U.S. Pat. No. 5,084,050, U.S. Pat. No. 5,720,753, U.S. Pat. No. 6,656,184, U.S. Pat. No. 6,517,542, and U.S. Pat. No. 6,835,206. Helical anchors are generally well known, for example, U.S. Pat. No. 806,406, U.S. Pat. No. 3,983,736, U.S. Pat. No. 4,536,115, U.S. Pat. No. 5,312,214, U.S. Pat. No. 6,276,883, U.S. Pat. No. 6,494,657, and U.S. Pat. No. 6,860,691. Furthermore, helically wound springs have been described for use as tissue anchors (WO 01/08602) and helical coils have been described for use as surgical implants (U.S. 2004/0225361).

BRIEF SUMMARY OF THE INVENTION

The present disclosure is directed to a fixation system used to supplement the fixation of an orthopedic implant. The optional fixation system includes a fixation structure that is inserted into the cancellous bone through a lumen in an orthopedic implant. The orthopedic implant and fixation system are intended to be implanted in the patient and remain in the patient indefinitely. The orthopedic implant and the fixation structure are typically separate and discrete structures that are releasably attached to permit future removal, revision, adjustment, and the like.

In many circumstances, the orthopedic implant is sufficiently secure in the bone such that no further fixation assemblies are required. If, however, the surgeon determines that the orthopedic implant is not sufficient stable, either during the current procedure or during a subsequent procedure, the insert can optionally be removed to expose the lumen. The present fixation system is then implanted and coupled to the orthopedic implant. The present approach provide the surgeon additional flexibility during the implantation procedure or during a later revision, without compromising the structural integrity of the orthopedic implant.

One embodiment is directed to a fixation system configured to releasably secure an orthopedic implant to a bone. The orthopedic implant has at least one lumen extending from a proximal portion to a distal portion configured to extend through cortical portions and into cancellous portions of the bone. The fixation system includes at least one expandable member configured to be inserted through the lumen and positioned in the cancellous bone near the distal portion of the orthopedic implant. The expandable member includes at least one chamber. A flowable biomaterial is delivered through the lumen and inflates the expandable member to an expanded configuration located in the cancellous bone. The expanded configuration includes at least one dimension greater than a corresponding dimension on the orthopedic implant to secure the orthopedic implant in the bone. An insert is secured in the lumen to releasably attach the fixation system to the orthopedic implant, such that the expandable member is detachable from the orthopedic implant to facilitate subsequent removal of the orthopedic implant from the bone. The biomaterial preferably acts to incorporate the expandable member into the cancellous bone.

The present fixation system provides the surgeon with the option to augment the fixation of an orthopedic implant, without compromising structural integrity of the implant. As a result, the breaking angle, torsion strength, torsion yield strength, insertion torque, self-tapping force, and maximum torque of the orthopedic implant combined with the insert, as measured according to ASTM standard F543-07-Standard Specification and Test Methods for Metallic Bone Screws, are comparable to the same orthopedic implant without the lumen and insert. Properly engineered, the breaking angle, torsion strength, torsion yield strength, insertion torque, self-tapping force, and maximum torque of the orthopedic implant combined with the insert are greater than the same orthopedic implant without the lumen and insert.

The present fixation system increases the pull out strength of the orthopedic implant, as measured ASTM standard F543-02 Annex A3 "Test Method for Determining the Axial Pullout Strength of Medical Bone Screws, by at least 20%, or at least 40%, or at least 70%, relative to the orthopedic implant alone.

In one embodiment, the expandable member is a porous structure with openings sized to permit intimate contact between the biomaterial and the cancellous bone. The expandable member is optionally a pre-determined volume and shape.

In one embodiment, the expandable member includes a neck portion configured to be secured to the orthopedic implant by the insert. The neck portion is preferably configured to be compressively engaged between the insert and an inside surface of the lumen. The expandable member and the neck portion are optionally a unitary woven structure. The insert is preferably the same insert used to seal the lumen in the orthopedic implant. A sleeve can optionally be used to guide the insert into the neck portion.

The biomaterial is preferably a curable biomaterial. A delivery tube is optionally configured to be inserted in the lumen and fluidly coupled to the expandable member to deliver a flowable biomaterial to the chamber. At least one check-valve assembly is optionally provided on the expandable member to receive the delivery tube and to retain the flowable biomaterial in the chamber after the delivery tube is removed. The biomaterial is preferably a resorbable, bone-growth stimulating composition that interacts with the cancellous bone through openings in the first expandable member. In another embodiment, the lumen of the orthopedic implant is used to deliver the biomaterial to the expandable member.

The delivery tube can be used to force the expandable member into the cancellous bone. In another embodiment, an inflatable device is provided to be inserted through the lumen in the orthopedic implant and expanded to prepare the cancellous bone to receive the expandable member. A biomaterial delivery system is provided to fluidly couple with a proximal end of the delivery tube to delivery the biomaterial under pressure to the chamber in the expandable member.

The expandable member optionally includes a plurality of fluidly coupled expandable members. A plurality of discrete expandable members of different sizes and shapes can be provided in a kit to provide the surgeon with options depending on the application.

Another embodiment is directed to an orthopedic implant configured to be implanted in a bone. The orthopedic implant includes at least one lumen extending from a proximal portion to a distal portion configured to extend through cortical portions and into cancellous portions of the bone. At least one fixation structure is configured to be inserted through the lumen and positioned in the cancellous bone near the distal portion of the orthopedic device. A flowable biomaterial configured to flow through the lumen to the cancellous bone and into engagement with the fixation structure. The flowable biomaterial and/or the fixation structure include at least one dimension greater than a corresponding dimension on the orthopedic device to secure the orthopedic device in the bone. An insert is configured to be secured in the lumen to releasably attach the fixation structure to the orthopedic device. The fixation structure is detachable from the orthopedic implant to facilitate subsequent removal of the orthopedic implant from the bone. In one embodiment, the biomaterial serves as the insert.

The fixation structure can be configured as one or more filaments, ribbon shaped structure, a sling, a braided structure, and the like. The fixation structure can be made from any of the material disclosed herein, including mono-filaments, woven or non-woven materials, mesh, porous and non-porous sheet materials, suture material, and the like.

Another embodiment is directed to an orthopedic implant configured to be implanted in a bone. The orthopedic implant includes at least one lumen extending from a proximal portion to a distal portion configured to extend through cortical portions and into cancellous portions of the bone. A fixation system is provided that includes at least one expandable member configured to be inserted through the lumen and positioned in the cancellous bone near the distal portion of the orthopedic device. The expandable member includes at least one chamber. A delivery tube is configured to be inserted in the lumen and fluidly coupled to the expandable member to deliver a flowable biomaterial to the chamber. A flowable biomaterial is provided that flows through the delivery tube and inflates the expandable member to an expanded configuration located in the cancellous bone. The expanded configuration includes at least one dimension greater than a corresponding dimension on the orthopedic device to secure the orthopedic device in the bone. An insert is secured in the lumen to releasably attach the fixation system to the orthopedic device, such that the expandable member is detachable from the orthopedic implant to facilitate subsequent removal of the orthopedic implant from the bone.

The insert is preferably configured to seal the lumen in the orthopedic device when the fixation system is not in use. The orthopedic device can be a bone screw, bone pin, intramedullary implant, acetabular implant, glenoidal implant, bone plate, or bone anchor.

The present disclosure is also directed to a method of implanting an orthopedic implant in a bone. The method includes implanting an orthopedic implant in the bone such that a proximal portion of the orthopedic implant is accessible, and a distal portion of the orthopedic implant extends through cortical portions and into cancellous portions of the bone. The surgeon then evaluates fixation of the orthopedic implant. If additional fixation is indicated, an insert is removed to expose at least one lumen extending from the proximal portion to the distal portion. At least one expandable member is inserted through the lumen and positioning the expandable member in the cancellous bone. A flowable biomaterial is delivered through the lumen and into the expandable member located in the cancellous bone. The expandable member is expanded to an expanded configuration with at least one dimension greater than a corresponding dimension on the orthopedic implant in the bone. The insert is secured in the lumen to releasably attach the fixation system to the orthopedic implant, such that the expandable member is detachable from the orthopedic implant to facilitate subsequent removal of the orthopedic implant from the bone.

The method includes bringing the biomaterial into intimate contact with the cancellous bone through openings in the expandable member. A neck portion on the expandable member is used to secure the fixation system to the orthopedic implant.

In one embodiment, an inflatable device is inserted through the lumen and into the cancellous bone. The inflatable device is inflated to prepare the cancellous bone to receive the expandable member.

BRIEF DESCRIPTION OF THE SEVERAL VIEWS OF THE DRAWING

FIGS. 2A through 2H illustrate a method of securing an orthopedic implant with a fixation system in accordance with an embodiment of the present disclosure.

FIGS. 4A through 4C illustrate methods of preparing cancellous bone to receive a fixation system in accordance with an embodiment of the present disclosure.

FIGS. 8A and 8B illustrate an alternate method of securing a fixation system to an orthopedic implant in accordance with an embodiment of the present disclosure.

FIG. 8C illustrates an alternate method of securing a fixation system to an orthopedic implant in accordance with an embodiment of the present disclosure.

FIG. 8D illustrates an alternate insert for securing a fixation system to an orthopedic implant in accordance with an embodiment of the present disclosure.

FIGS. 9A and 9B illustrate an insert secured at both ends of an orthopedic implant in accordance with an embodiment of the present disclosure.

FIGS. 12A and 12B illustrate a method of deploying a fixation system with a plurality of expandable members in accordance with an embodiment of the present disclosure.

FIG. 13 illustrates a modular fixation system with a plurality of expandable members in accordance with an embodiment of the present disclosure.

FIGS. 18A and 18B illustrate a combination bone anchor-tissue anchor and fixation system in accordance with an embodiment of the present disclosure.

FIG. 19 illustrates an adjustable tissue anchor and fixation system in accordance with an embodiment of the present disclosure.

FIGS. 20A through 20C illustrate use of a sleeve to guide an insert into engagement with an expandable member in accordance with an embodiment of the present disclosure.

FIGS. 21A through 21C illustrate the use of the biomaterial as an insert to secure a fixation system to an orthopedic implant in accordance with an embodiment of the present disclosure.

FIGS. 23A and 23B illustrate an alternate insert for securing an expandable member to an orthopedic implant in accordance with an embodiment of the present disclosure.

FIG. 25 illustrates an alternate fixation structure for an orthopedic implant in accordance with an embodiment of the present disclosure.

FIG. 26A illustrates and insert and fixation structure for use with an orthopedic implant in accordance with an embodiment of the present disclosure.

FIG. 26B illustrates an orthopedic implant with the insert and fixation structure of FIG. 26A.

DETAILED DESCRIPTION OF THE INVENTION

Figure 1:
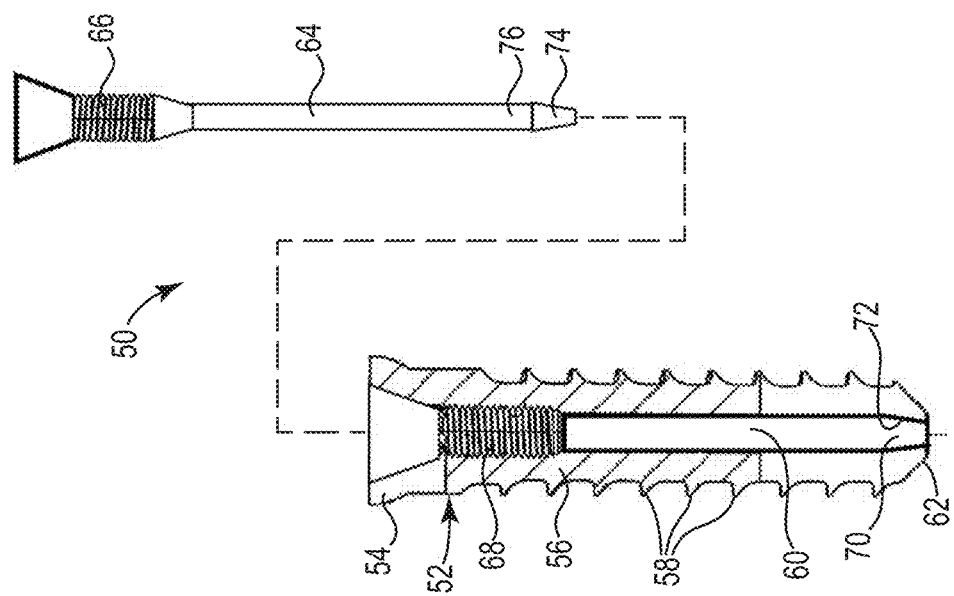
FIG. 1 illustrates an orthopedic implant for use with a fixation system in accordance with an embodiment of the present disclosure.

FIG. 1 is a side view of an orthopedic implant 50 configured for use with an optional fixation system 98 (see FIG. 2E) in accordance with an embodiment of the present disclosure. The orthopedic implant 50 is preferably a discrete, independently functioning structure that can be implanted in a patient, without the fixation system 98. The fixation system 98 is typically included only on an as needed basis as determined by the surgeon. The present fixation system functions as an optional add-on for a variety of orthopedic implants.

In the illustrate embodiment, the orthopedic implant 50 is a cannulated bone screw 52 having a head 54, a shank 66 with threads 58. Lumen 60 extends from the head 54 to distal end 62. Insert 64 includes threads 66 configured to engage with internal threads 68 in the head 54. In the illustrated embodiment, distal end 70 of the lumen 60 includes tapered portion 72 that corresponds with tapered portion 74 at the distal end 76 of the insert 64. When located in the orthopedic implant 50, the insert 64 substantially seals the lumen 60 (see FIG. 2). Cannulated bone screws used for common orthopedic applications typically have diameters in the range of about 2.5 millimeters to about 8 millimeters, with a lumen diameter in the range of about 1.3 millimeters to about 3.5 millimeters. Length of the bone screw varies with application.

The orthopedic implant 50 can be constructed from a variety of biocompatible materials such as titanium, titanium alloys, 316L stainless steel, cobalt chrome alloys and non-absorbable and absorbable polymers as known in the art. The implantable implant 50 may be coated with a porous and bioactive material or a combination thereof to allow bone growth onto the device and to promote bone growth into any notches or other openings or spaces surrounding the device (collectively bone in-growth). For example, one or more of hydroxyapatite, bone morphogenic protein-2 (BMP-2), retinoic acid and biophosphonates may enhance bone in-growth. Alternatively, the surface of the device could be porous to similarly encourage bone growth and promote fixation of the device within the bone.

Figure 2A:
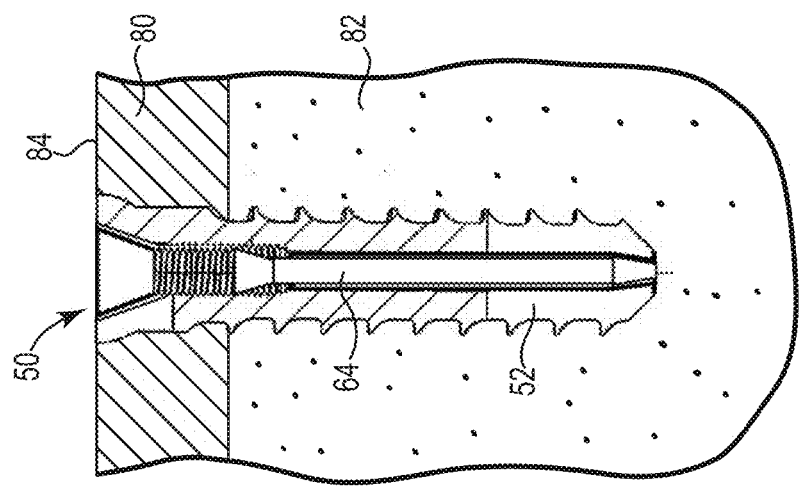

FIGS. 2A through 2H illustrate a sequence for using the orthopedic implant 50 in accordance with an embodiment of the present disclosure. FIG. 2A illustrates the bone screw 52 extending through cortical bone 80 and into the considerably softer and sponge-like inner cancellous bone 82 of the bone 84. The insert 64 reinforces the cannulated bone screw 52 so that it has comparable torsion and bending strength of a non-cannulated bone screw. In particular, the breaking angle, torsion strength, torsion yield strength, insertion torque, self-tapping force, and maximum torque of the bone screw 52 combined with the insert 64, as measured according to ASTM standard F543-07-Standard Specification and Test Methods for Metallic Bone Screws, are comparable to the same bone screw 52 without the lumen 60 and the insert 64.

In many circumstances, the bone screw 52 is sufficiently secure in the bone 84 such that no further fixation assemblies are required. If, however, the surgeon determines that the bone screw 52 is not sufficient stable, either during the current procedure or during a subsequent procedure, the insert 64 can optionally be removed to expose the lumen 60 as illustrated in FIG. 2B. The present approach provides the surgeon additional flexibility during the implantation procedure or during a later revision, without compromising the structural integrity of the orthopedic implant 50.

Figure 2C:
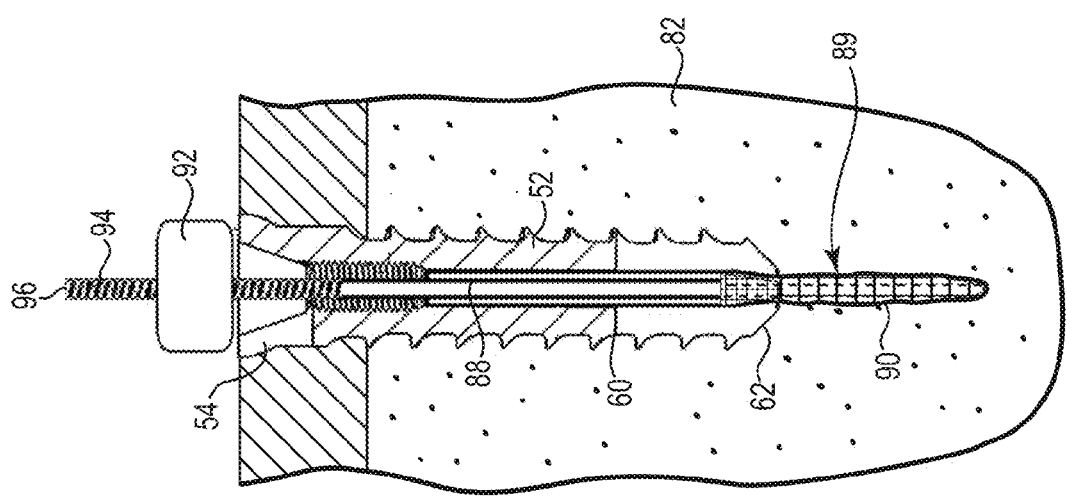
Figure 2B:
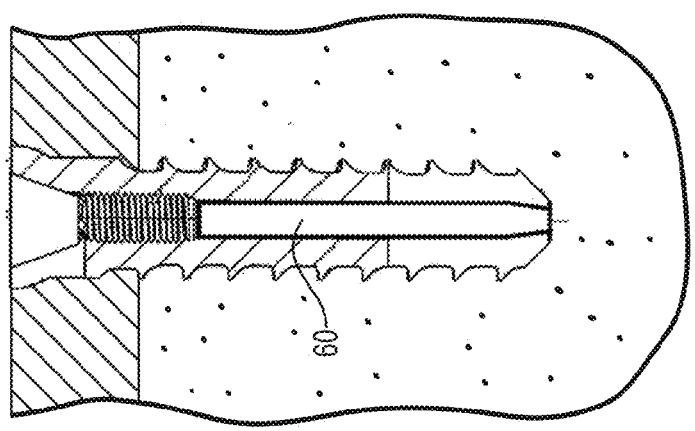

FIG. 2C illustrates inserting fixation structure 89 through the lumen 60 and into the cancellous bone 82. The fixation structure can be any biocompatible material that is designed to be retained in cancellous bone by a biomaterial, such as the expandable member 90 discussed herein. In many applications, the fixation structure substantially retains the biomaterial, while permitting intimate contact with the cancellous bone. In applications where flow of the biomaterial is not a concern, a cavity in the cancellous bone can be used to retain the biomaterial and the fixation structure can assume any configuration suitable for engaging with the biomaterial, such as for example, a sling, a filament, a barbed structure, and the like. The fixation structure is embedded in the biomaterial and the biomaterial preferably creates a mechanical interlock with the bone. In some embodiments, the biomaterial bonds with, or is incorporated into, the bone, increasing the fixation strength.

In the illustrated embodiment, the fixation structure 89 is a flexible expandable member 90 supported by delivery tube 88. Stop 92 is engaged with threads 94 at proximal end 96 of the delivery tube 88 to limit how far the expandable member 90 is inserted into the cancellous bone 82. If necessary, the proximal end 96 of the delivery tube 88 can be gently tapped with a hammer until the stop 92 engages the head 54. For use in a bone screw, the delivery tube 88 has an inside lumen typically with a diameter in the range of about 1.0 millimeters to about 3.0 millimeters. For use in an intramedullary application, the delivery tube 88 can have a significantly larger lumen diameter.

As illustrated in FIG. 2C, the delivery tube 88 is preferably advanced beyond the distal end 62 of the bone screw 52 in order to position the expandable member 90 in the cancellous bone 82, and to position the expandable member 90 relative to the bone screw 52. In alternate embodiments, a cavity is formed in the cancellous bone 82 to facilities positioning the expandable member 90 (see e.g., FIGS. 4A-4C).

The delivery tube 88 may be constructed from a variety of metal or polymeric materials and can be flexible or rigid depending on the application. In one embodiment, the delivery tube 88 has sufficient column stiffness to displace and compress the cancellous bone 82. In another embodiment, a stylet is inserted into the delivery tube 88 to augment the column stiffness of the delivery tube 88 during insertion into the cancellous bone 82, and then subsequently removed to permit delivery of the biomaterial 100.

As illustrated in FIG. 2D, the delivery tube 88 is preferably retracted a sufficient amount so that the distal end 102 of the delivery tube 88 does not interfere with the delivery of the biomaterial 100. The biomaterial 100 is then delivered through the delivery tube 88 to fill chamber 104 and at least partially inflate the expandable member 90. In this context, the term inflate generally means to distend, swell, or expand a flexible structure with a fluid.

In the preferred embodiment, the delivery pressure of the biomaterial 100 is sufficient to compress the adjacent cancellous bone 82 as the expandable member 90 is filled. In the expanded configuration 108 illustrated in FIG. 2D, the expandable member 90 and the biomaterial 100 preferably substantially fill, and conform to, the shape of, the cavity 106.

In one embodiment, the expandable member 90 has a shape generally conforming to the shape of the cavity 106 and the biomaterial 100. In another embodiment, the expandable member 90 is embedded in the biomaterial 100, but does not have a shape that corresponds to the shape of the cavity 106.

Once delivery of the biomaterial 100 is completed, the delivery tube 88 is withdrawn, as illustrated in FIG. 2E. Neck portion 110 of the expandable member 90 is positioned in the lumen 60 at the taper 72. The fixation system 98 is now ready to be secured to the fastener 52.

As illustrated in FIGS. 2F and 2G, the insert 64 is reintroduced into the lumen 60. The threads 66, 68 advance the distal end 76 of the insert 64 into engagement with the neck portion 110 of the expandable member 90. In one embodiment, the neck portion 110 has a generally stiff cone-shape corresponding to the tapered portions 72, 74. The neck portion 110 is preferably constructed from a stiff material that retains its shape. When the insert 64 is securely coupled to the fastener 52, the tapered portion 74 on the insert 64 compressively engages the neck portion 110 against the tapered portion 72 at the distal end 62 of the lumen 60.

The expanded configuration 108 increases the fixation of the bone screw 52 simply by increasing the surface area of engagement with the cancellous bone 84. Fixation is also increased by the shape of the expandable member 90 in the expanded configuration 108.

In one embodiment, the expanded configuration 108 of the expandable member 90 includes has at least one dimension 113 greater than a corresponding dimension 112 of the bone screw 52. Corresponding dimension refers to dimensions or features located along an axis of failure (e.g., pull-out direction 118B) of both an orthopedic implant and a fixation system. The at least one dimension 113 reduces the risk that the fixation system 98 will be pulled through the opening 114 in the cortical bone 80. In particular, the expanded configuration 108 increases the pull-out strength of the bone screw 52, as measured according to ASTM standard F543-02 Annex A3 "Test Method for Determining the Axial Pullout Strength of Medical Bone Screws, which is incorporated by reference.

The transverse dimension 113 (perpendicular to an axis of the lumen 60) of the expandable member 90 and the biomaterial 100 is preferably greater than the transverse dimension of the bone screw 52. In one embodiment, the transverse dimension 113 is at least 125%, and more preferably at least 150%, of the transverse dimension 112 of the bone screw 52.

Enlarged lower surface 116 of the expandable member 90 augments the fixation of the bone screw 52 against compression force 118A. Enlarged upper surface 120 augment the fixation of the bone screw 52 against tension force 118B. The attachment of the neck portion 110 to the distal end 62 transfers the compression and tension forces 118A, 118B between the expandable member 90 and the bone screw 52.

The fixation system 98 also effectively resists bending moments 118C. In embodiments where the expandable member 90 deploys in a non-symmetrical shape, the present orthopedic implant 50 resists torques 118D applied to the bone screw 52, reducing the risk of the screw 52 backing itself out over time.

The fixation system 98 provides the surgeon with the option to augment the fixation of the bone screw 52, without compromising structural integrity. The fixation system 98 preferably increases the pull out strength in direction 118B of the bone screw 52, as measured ASTM standard F543-02 Annex A3 "Test Method for Determining the Axial Pullout Strength of Medical Bone Screws, by at least 20%, or at least 40%, or by at least 70%, relative to the bone screw 52 alone. Pull out strength refers to the tensile force in direction 188B required to fail or remove the bone screw 52 from the bone 84.

In one embodiment, the biomaterial 100 quickly cures or hardens in-situ to provide immediate supplemental fixation to the bone screw 52. As used herein, the term "cure" and inflections thereof, will generally refer to any chemical transformation (e.g., reacting or cross-linking), physical transformation (e.g., hardening or setting), and/or mechanical transformation (e.g., drying or evaporating) that allows the biomaterial to change or progress from a first physical state or form (generally liquid or flowable) that allows it to be delivered to the site, into a more permanent second physical state or form (generally solid) for final use in vivo. When used with regard to the method of the present disclosure, for instance, "curable" can refer to uncured biomaterial, having the potential to be cured in vivo (as by catalysis or the application of a suitable energy source), as well as to the biomaterial in the process of curing.

It is not necessary for the biomaterial 100 to harden or cure for the fixation system 98 to secure the bone screw 52. The fixation system 98 captures the bone screw 52 within the cancellous bone 82 to resist tension force 118B and bending moment 118C. The biomaterial 100 is preferably a substantially incompressible material located within a fixed space (i.e., cavity 106), to resist compression force 118A. In embodiments where the biomaterial 100 does not cure or harden in-situ, the patient may require an external structure, such as a brace or cast, to secure the bone 84 until sufficient bone in-growth occurs.

Even after implantation, the fixation system 98 remains separable from the bone screw 52. As illustrated in FIG. 2H, if the bone screw 52 needs to be removed from the bone 84 for any reason, the insert 64 is simply removed to release the neck portion 110 from the bone screw 52. In the event that there is residual adhesion between the neck portion 110 and the bone screw 52, an instrument such as a probe, drill, trocar can be inserted into the lumen 60 as illustrated in FIG. 2IC.

The bone screw 52 is then removed from the bone 84 by rotating in the counter-clockwise direction 111. The implanted fixation system 98 can be reused or abandoned in the bone 84. In an embodiment where the biomaterial 100 is a bioabsorbable bone growth material, the fixation system 98 is substantially absorbed into the bone 84.

The fixation structures disclosed herein, including expandable member 90, can be constructed from elastic or inelastic materials that provide an optimal combination of such properties as flexibility under static and dynamic conditions, tensile strength, elongation, tensile modulus, ductility, stability and durability, and compliance. In one embodiment, the expandable member 90 has a pre-determined volume and shape corresponding to the implantation site, such as disclosed in U.S. Pat. No. 5,972,015 (Scribner et al.), which is hereby incorporated by reference.

In another embodiment, the lateral walls of the expandable member 90 are constructed from a compliant material (or having a compliance value significantly lower than the delivery pressure of the biomaterial 100 so as to stretch) and the superior and inferior walls 120, 116 are non-compliant material (or having a compliance value significantly higher than the delivery pressure of the biomaterial 100). Consequently, during delivery of the biomaterial 100, the expansion force is essentially applied in lateral direction 122 (outward relative to the axis of the bone screw 52) to create a flattened oval shape. This configuration increases the size of the upper and lower surfaces 120, 116 to increase fixation.

In one embodiment, the expandable member 90 is constructed from a flexible porous material with pore sizes sufficient to generally retain the biomaterial 100, but also permit intimate contact between the biomaterial 100 and the cancellous bone 82, such as for example, the biocompatible mesh disclosed in U.S. Pat. No. 7,226,481 (Kuslich) and U.S. Patent Publication No. 2009/0024147 (Ralph et al.), which are hereby incorporated by reference. In one embodiment, the expandable member 90 includes pores in the range of about 0.25 millimeters to about 5.0 millimeters. The size of the pores are determined based on a number of factors, such as the viscosity of the biomaterial 100, the maximum delivery pressure of the biomaterial 100, and the like.

In another embodiment, the expandable member 90 is embedded in the biomaterial 100. For example, the pore sizes permit the biomaterial 100 to flow freely into the cavity 106 and the cavity 106 retains the biomaterial 100.

In one embodiment, the expandable member 90 is a continuous film with a plurality of hole. In order to maximize the contact between the biomaterial 100 and the cancellous bone 82, the number of openings is preferably maximized, while the size of an individual opening is limited to retain the biomaterial 100 in the expandable member 90

The expandable member 90 may be a woven or non-woven structure made from metal or polymeric fibers. Suitable metals include titanium or one of its alloys, or stainless steel. Suitable polymeric materials include polymethyl methacrylate (PMMA), castable thermoplastic polyurethanes, for instance those available under the tradenames CARBOTHANE (Thermedics) ESTANE (Goodrich), PELLETHANE (Dow), TEXIN (Bayer), Roylar (Uniroyal), and ELASTOTHANE (Thiocol), as well as castable linear polyurethane ureas, such as those available under the tradenames CHRONOFLEX AR (Cardiotech), BIONATE (Polymer Technology Group), and BIOMER (Thoratec).

In one embodiment, the expandable member 90 is coated with an osteo-conductive tissue scaffold, such as disclosed in U.S. Patent Publication Nos. 2011/0082564 (Liu et al.) and 2010/0268227 (Tong et al.), which are hereby incorporated by reference. The expandable member 90 and/or the biomaterial 100 optionally include radiopaque properties. Various configurations of a porous expandable structure are disclosed in U.S. Pat. No. 5,549,679 (Kuslich), which is incorporated by reference.

In alternative embodiments, the expandable member 90 may also be formed out of shape memory alloys (SMA) such as nickel titanius (NiTi) shape memory alloys (Nitinol), whereby the expandable member 90 can be programmed to be in the contracted state at one temperature (i.e. either below or above body temperature) and in the expanded state at or around body temperature. Thus, potentially allowing for self-expansion at a desired target site by merely allowing the expandable member 90 to come to body temperature. The low elastic modulis, high fatigue, ductile and high resistance to wear of NiTi alloys are particularly useful for the present expandable member 90.

The biomaterial 100 can be any flowable biocompatible material that can be delivered through delivery tube 88. In the preferred embodiment, the biomaterial 100 is a resorbable, bone-growth stimulating composition that interacts with the cancellous bone 82 through the porous expandable member 90. Bone in-growth preferably extends substantially through the chamber 104 of the expandable member 90 so that the biomaterial 100 is all eventually incorporated into the cancellous bone 82.

In one embodiment, the biomaterial 100 is small fragments of an osteogenic sponge composition having enhanced osteoinductive properties for use in bone repair, such as disclosed in U.S. Patent Publication Nos. 2002/0082694 (McKay) and 2010/0255042 (Jennissen et al.), which are incorporated by reference. The fragments of sponge composition are sufficient small and compressible to fit into the lumen of the delivery tube 88. The composition enables increased osteoinductive activity while retaining a reliable scaffold for the formation of new bone within the chamber 104 of the expandable member 90. Various bioactive load bearing bone graft compositions suitable for use as the present biomaterial 100 are disclosed in U.S. Pat. No. 5,681,872 (Erbe); U.S. Pat. No. 5,914,356 (Erbe); and U.S. Pat. No. 7,589,133 (Pomrink), which are hereby incorporated by reference. A calcium phosphate bone void filler sold under the tradename OsteoVationEX available from Osteomed of Addison, Tex., is suitable for use as the present biomaterial 100.

The osteogenic factor can be one that stimulates production or activity of osteoblasts and osteoclasts. The factor is preferably a bone morphogenetic protein (BMP) or a LIM mineralization protein (LMP), or comprises a nucleotide sequence encoding a BMP or LMP. Recombinant human BMPs may be commercially obtained or prepared as described and known in the art, e.g. in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al., which are hereby incorporated by reference. Such osteogenic factors are preferably delivered in conjunction with cells, for example autologous cells from the recipient of the implant. Most preferably the vector is delivered in conjunction with autologous white blood cells derived from bone marrow or peripheral blood of the recipient. These cells may be applied to the sponge composition along with the osteogenic factor prior to implantation.

The biomaterial 100 may be in the form of a flowable putty or paste, such as the bone-growth stimulating composition, such as disclosed in U.S. Patent Publication No. 2006/0204586 (Alexander et al.) and U.S. Pat. No. 7,172,629 (McKay), which are hereby incorporated by reference. U.S. Pat. No. 6,770,695 (Ricci et al.) discloses a bone growth stimulating material with a controlled resorption rate that includes a calcium sulfate compound and a polymer containing particles with a setting agent that is flowable through the delivery tube 88. The biomaterial 100 optionally includes radiopaque properties to facilitate imaging. Injectable compositions suitable for use as the biomaterial 100 is disclosed in U.S. Patent Publication Nos. 2012/0225972 (Guillermo et al.); 2012/0195982 (Hu); 2012/0107401 (McKay); and 2012/0095463 (Rains et al.), which are hereby incorporated by reference.

In another embodiment, the biomaterial 100 is a flowable carrier matrix including collagen sponge, ranging from 1.0 mm to 10 mm in size, wetted with a fluid, such as morphogen, such as disclosed in U.S. Pat. No. 7,671,014 (Beals et al.), which is hereby incorporated by reference. A bulking material may be added to the carrier matrix, such as for example collagen-ceramic composite materials, allograft and biocompatible ceramics or minerals that provide bone in-growth scaffolding.

While not preferred, the biomaterial 100 may also be a bone cement. By locating the expandable member 90 distally from the fastener 52 the integrity of the bone 84 engaged with the threads 58 is not compromised.

The biomaterial 100 may also be an in situ curable polymeric materials including, for example, elongated polymeric materials, polymeric beads, hydrogel materials, fusion promoting materials, autograft bone, allograft bone, xenograft bone, or any combination thereof. The biomaterial 100 is preferably bioresorbable, such as for example, poly(lactic acid), poly(glycolic acid), p-dioxanon fibers, polyarylethyl, polymethyl methacrylate, polyurethane, amino-acid-derived polycarbonate, polycaprolactone, aliphatic polyesters, calcium phosphate, unsaturated linear polyesters, vinyl pyrrolidone, polypropylene fumarate diacrylate, or mixtures thereof, or other biocompatible compounds. A flowable, biodegradable polymer that cures in-situ suitable for use as the biomaterial 100 is disclosed in U.S. Pat. No. 5,990,194 (Dunn et al.), which is hereby incorporated by reference. The biomaterial 100 may also be particles, such as bone graft material, bioceramic beads, and/or crushed bone, and associated delivery device disclosed in U.S. Pat. No. 6,620,162 (Kuslich et al.), which is incorporated by reference.

Figure 3:
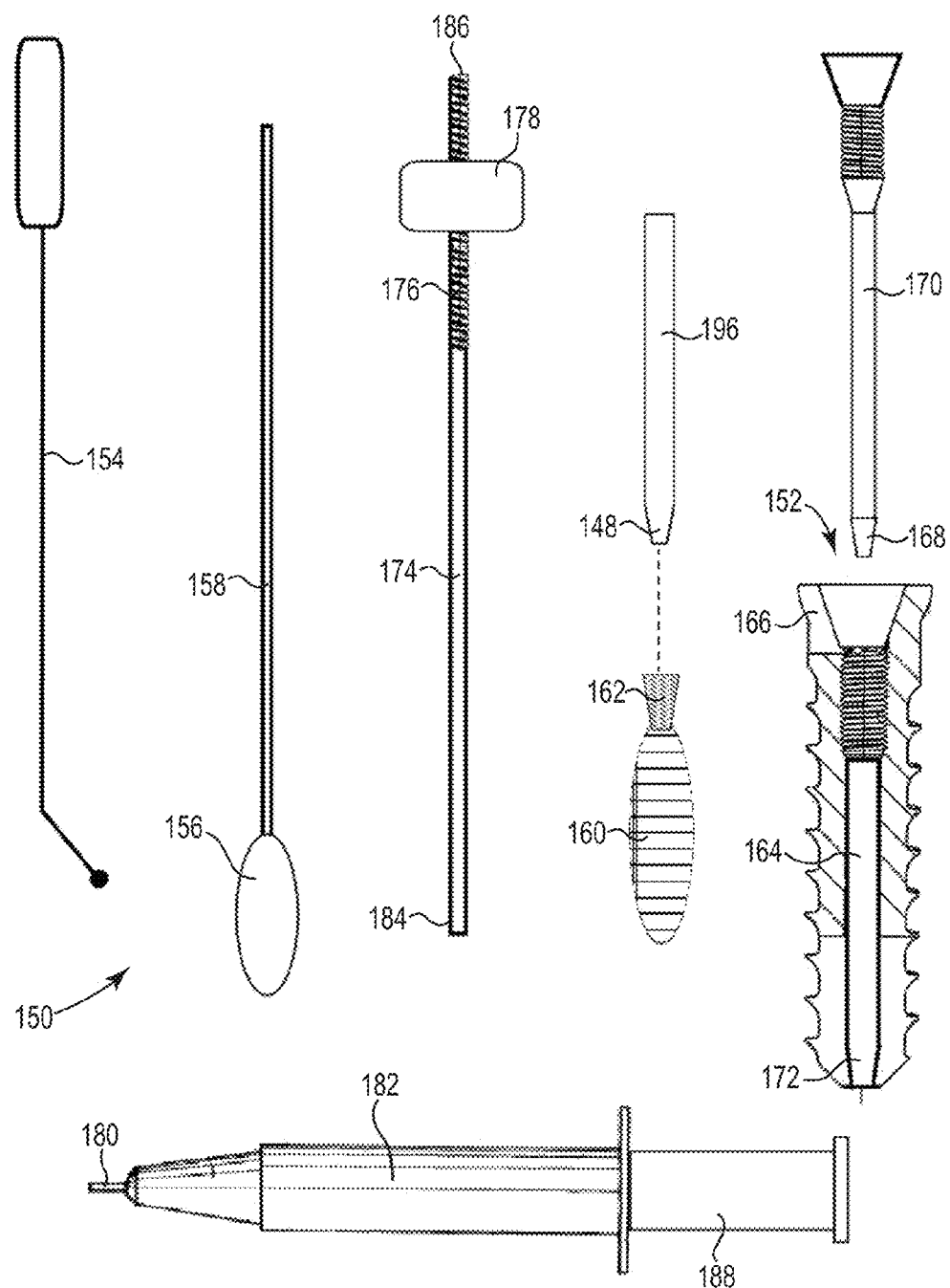
FIG. 3 is a schematic illustration of a kit for a fixation system in accordance with an embodiment of the present disclosure.

FIG. 3 illustrates a kit 150 for use with an orthopedic implant 152 in accordance with an embodiment of the present disclosure. The kit 150 includes a probe 154 and a inflatable device 156 with an attached fill tube 158, both used to preform a cavity in the cancellous bone to receive expandable member 160. In some embodiments, the probe 154 can be configured as an expandable drill bit, such as disclosed in U.S. Pat. No. 5,693,011 (Onik) and U.S. Pat. No. 5,928,239 (Mirza), which are hereby incorporated by reference. These expandable drill bits permit the formation of a cavity with an undercut so that the fixation structure has a dimension greater than a corresponding dimension of the opening in the cortical bone along the axis of the pull-out direction.

The expandable device 160 includes neck portion 162 constructed from a material with sufficient stiffness to retain its shape when positioned in lumen 164 of the fastener 166. The neck portion 162 preferably includes a shape complementary to the shape of the tip 168 on the insert 170 and distal opening 172 of the lumen 164.

Optional sleeve 196 includes a distal end 198 sized to fit inside the neck portion 162 (see e.g., FIG. 20B). The sleeve 196 has a diameter to fit in the lumen 164 and serves to guide the tip 168 into the neck portion 162. See FIG. 20C.

In one embodiment, the neck portion 162 is constructed from the same porous material used to construct the expandable member 160, but is treated with a supplemental material, such as a biocompatible polymer, to increase stiffness. In another embodiment, the neck portion 162 is heat treated to increase stiffness.

Delivery tube 174 preferably includes threaded proximal end 176 to position stop 178 along its axial length to prevent the distal end 184 from penetrating too far into the bone. The proximal end 176 also includes an opening 186 sized to receive tip 180 of biomaterial injection system 182 containing the biomaterial 100. In one embodiment, the biomaterial injection system 182 is configured with a quantity of biomaterial 100 corresponding to the volume of the expandable member 160. Alternate biomaterial injection systems are disclosed in U.S. Pat. No. 7,544,196 (Bagga et al.) and U.S. Pat. No. 8,128,632 (Paris et al.), which are hereby incorporated by reference. Various adapters for coupling a biomaterial injection system to an orthopedic device are disclosed in U.S. Pat. No. 8,231,632 (Jordan et al.), which is hereby incorporated by reference.

FIGS. 4A-4C illustrate various methods of using the kit 150. FIG. 4A illustrates a method of using the probe 154 provided from the kit 150 to prepare cavity 190 in the cancellous bone 82. After removing the insert 170, the probe 154 is inserted through the lumen 164. The bend 194 preferably flexes to permit the probe 154 to fit in the lumen 164. The probe 154 is rotated and otherwise manipulated so that tip 192 prepares cavity 190 in cancellous bone 82. As used herein, "prepare" refers to compressing, fracturing, cut, drill, displacing, puncturing, and/or remove cancellous bone to at least partially form a cavity to receive a fixation system.

The expandable member 160 is then positioned on distal end 184 of the delivery tube 174 and inserted through the lumen 164, as discussed herein. Tip 180 of the biomaterial injection system 182 is fitted on the opening 186, and the plunger 188 is advanced to force biomaterial 100 into the expandable member 160. In some embodiments, the pressure of the biomaterial 100 is sufficient to form and/or increase the size of the cavity 190. The delivery tube 174 is removed and the insert 170 is reengaged with the fastener 166.

FIG. 4B illustrates a method of using the inflatable device 156 provided with the kit 150 to prepare the cavity 190 in the cancellous bone 82. The inflatable device 156, such as for example a balloon catheter, is delivered through the lumen 164 and positioned in the cancellous bone 82. The delivery tube 158 is used to inflate the inflatable device 156 and to form the cavity 190, such as disclosed in U.S. Pat. No. 6,235,043 (Reiley et al.), which is hereby incorporated by reference. The inflatable device 156 is preferably inflated with a liquid, and the volume of liquid is used as an estimate of the amount of biomaterial 100 required to fill the expandable member 160 and the cavity 190. The liquid and the inflatable device 156 are then removed from the lumen 164 and the expandable member 160 is implanted using any of the methods disclosed herein.

FIG. 4C illustrate an alternate embodiment in which the inflatable device 156 is positioned in the expandable member 160 to form the cavity 190 in accordance with an embodiment of the present disclosure. The inflatable device 156 is positioned inside the expandable member 160 and the assembly is simultaneously delivered through the lumen 164 and into the cancellous bone 82.

The inflatable device 156 is preferably inflated with a liquid, which simultaneously forms the cavity 190 and expands the expandable member 160. The liquid and the inflatable device 156 are then removed from the expandable member 160 and the fastener 166. The delivery tube 174 is inserted through the lumen 164 and into the expandable member 164 to deliver the biomaterial 100. Finally, the delivery tube 174 is removed and the insert 170 re-engaged with the fastener 166 as discuss herein.

Figure 5:
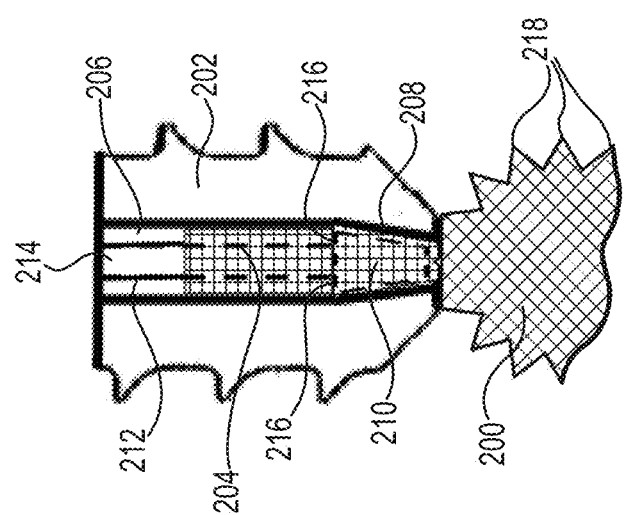
FIG. 5 illustrates an alternate fixation system with engagement features in accordance with an embodiment of the present disclosure.

FIG. 5 illustrates an alternate method of coupling an expandable member 200 to a fastener 202 in accordance with an embodiment of the present disclosure. Neck portion 204 extends up into lumen 206 beyond tapered portion 208 of the fastener 202. In one embodiment, distal end 210 of the insert 212 has a diameter greater than shaft 214 so that edges 216 facilitate engagement with the neck portion 204. During removal of the insert 212 during a revision procedure, the edges 216 preferably sever the neck portion 204 near the tapered portion 208 of the fastener 202.

In the illustrated embodiment, the expandable member 200 includes engagement features 218 that penetrate the adjacent cancellous bone 82 during delivery of the biomaterial 100. The delivery pressure of the biomaterial 100 is preferably sufficient to embed the engagement features 218 in the adjacent cancellous bone 82.

Figure 6:
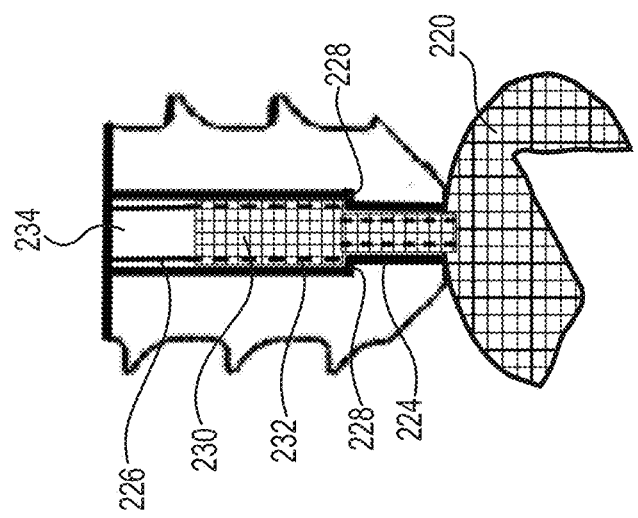
FIG. 6 illustrates an alternate structure for securing a fixation system to an orthopedic implant in accordance with an embodiment of the present disclosure.

FIG. 6 illustrates an alternate method of coupling an expandable member 220 to a fastener 222 in accordance with an embodiment of the present disclosure. Distal portion 224 of the lumen 226 includes shoulders 228. The neck portion 230 optionally has a shape corresponding to the shoulders 228 or is deformed into that shape when inserted in the lumen 226. Distal end 232 of the insert 234 includes a corresponding shape that captures the neck portion 230 against the shoulders 228.

Figure 7C:
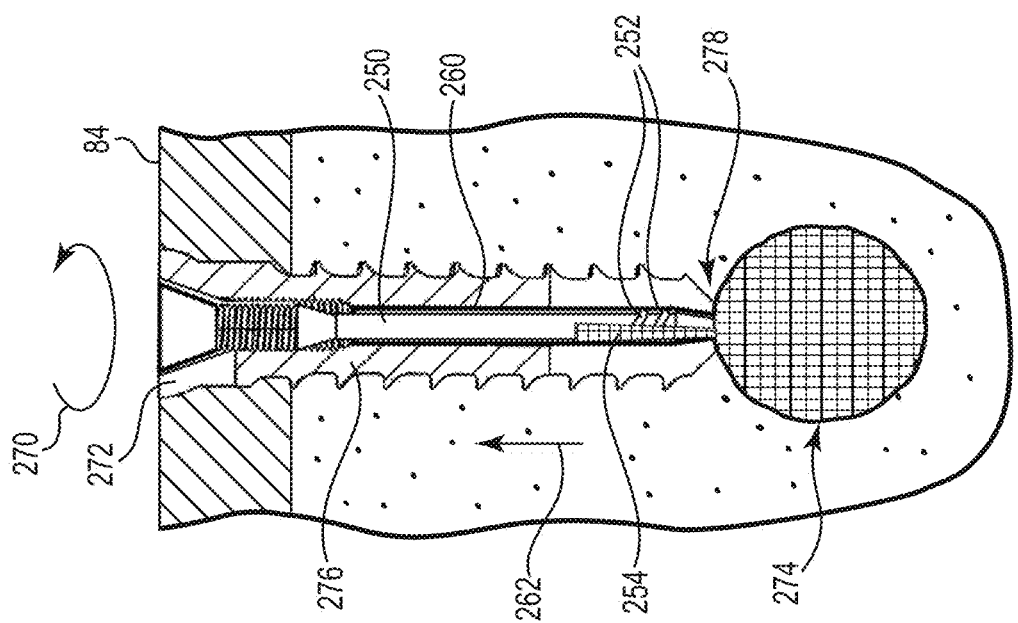
FIGS. 7A through 7C illustrate an alternate orthopedic implant with a fixation system in accordance with an embodiment of the present disclosure.
Figure 7B:
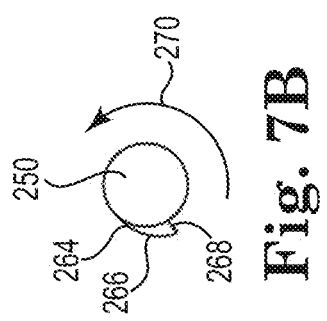
Figure 7A:
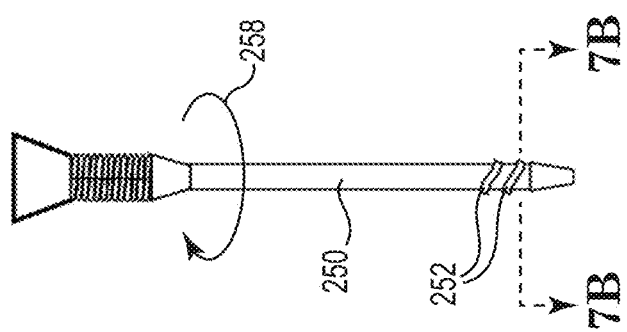

FIGS. 7A through 7C illustrate an alternate insert 250 with structure 252 configured to engage with neck portion 254 of the expandable member 256. In the illustrated embodiment, the structure 252 has a generally helical shape so that as the insert 250 is rotated in the clockwise direction 258, the neck portion 254 is drawn upward in direction 262 into the lumen 260 and slack is removed from the neck portion 254. Tension at interface 278 between the fastener 276 and the expandable member 256 increases fixation. FIG. 7C illustrates the neck portion 254 cut-away to show the structure 252.

Leading edge 264 of the helical structure 252 has a gradual slope so as to not damage the neck portion 254. Trailing edge 266 of the structure 252 preferably include cutting edge 268. If removal of the fastener 276 is required, the insert 250 is rotated in the counter-clockwise direction 270. Cutting edge 268 severs the neck portion 254 of the fixation system 274 to facilitate removal of the fastener 276 from the bone 84.

The present insert 250 with the cutting edge 268 permits the neck portion 254 to extend the entire length of the fastener 268. In one embodiment, the neck portion 254 extends beyond the head 272 of the fastener 276 (see e.g., FIG. 8B). After the insert 250 is engaged with the fastener 268 the excess neck portion 254 is cut and removed.

FIGS. 8A and 8B of an orthopedic implant 280 for use with fixation system 299 in accordance with an embodiment of the present disclosure. The expandable member 282 includes neck portion 284 that extends beyond head 286 of the fastener 288.

As illustrated in FIG. 8A, the insert is removed and the expandable member 282 and delivery tube 290 are inserted through the lumen 292. Check valve 294 is located generally between the expandable member 282 and the neck portion 284. The check-valve 294 serves to retain the biomaterial 100 (see FIG. 8B) in the expandable member 282 and/or prevent the biomaterial 100 from entering the lumen 292. The delivery tube 290 extends through the check valve 294 to delivery biomaterial 100 to the expandable portion 282.

In one embodiment, the neck portion 284 is modified to make it non-porous so that the biomaterial 100 does not contact the orthopedic implant 280. For example, the porous neck portion 284 can be coated with a polymeric material.

After delivery of the biomaterial 100 is completed, the delivery tube 290 is removed from the fastener 288. The check-valve 294 retains the biomaterial 100 in the expandable member 282 and prevents bonding with the orthopedic implant 280.

In one embodiment, insert 296 attaches proximal end 298 of the elongated neck portion 284 to the orthopedic implant 280. Any excess neck portion 284 extending above the head 286 is removed. In another embodiment, the inserts 170 or 250 can be used to secure the expandable member 282 to the fastener 288.

The orthopedic implant 280 can be removed from the bone 84 by removing the insert 296, 170, 250. In one embodiment, the insert 250 (see FIG. 7A) is engaged with the fastener 288. As the insert 250 is disengaged the cutting edge 268 (see FIG. 7A) severs the neck portion 284. In another embodiment, a cutting tool, such as a drill bit or trocar such as illustrated in FIG. 21C, is inserted into the lumen 292 to sever the neck portion 284 from the expandable member 282.

In another embodiment, the check valve 294 is omitted. If the biomaterial 100 bonds to the sidewalls of the lumen 292, removal can be accomplished by running a cutting tool down the lumen 292 as illustrated in FIG. 21C.

FIG. 8C illustrates an alternate method of securing the fixation system 299 to the fastener 288. A tension force 297 is applied to the neck portion 284 to pull the proximal end 298 to one side, exposing threads 295. The tension force 297 reduces any slack in the neck portion 284. The insert 296 is then engaged with the threads 295 to secure the neck portion 284 to the fastener 288.

FIG. 8D illustrates an alternate method of securing the fixation system 299 to the fastener 288. Insert 293 is inserted into the neck portion 284. Tip 291 of the insert 293 acts to drive biomaterial 100 in the neck portion 284 into the expandable portion 282. The check valve 294 is not required in this embodiment. The fastener 288 can be removed from the bone 84 using the methods disclosed in connection with FIG. 8B.

FIG. 9A is a side view of an alternate orthopedic implant 300 for use with fixation system 332 (see FIG. 9B) in accordance with an embodiment of the present disclosure. In the illustrate embodiment, the orthopedic implant 300 is a cannulated fastener 302 having a head 304, a shank 306 with threads 308. Lumen 310 extends from the head 304 to distal end 312. Insert 314 includes threads 316 configured to engage with internal threads 318 near distal end 312 of the lumen 310.

Locking screw 322 engaged with internal threads 324 located in the head 304 of the fastener 302 in order to torsionally lock the head 320 of the inssert 314 to the fastener 302. When located in the orthopedic implant 300, the inssert 314 substantially seals the lumen 310 (see FIG. 9B).

The inssert 314 is configured to torsionally couple to both the head 304 and the distal end 312 of the fastener 302. Consequently, the breaking angle, torsion strength, torsion yield strength, insertion torque, self-tapping force, and maximum torque of the fastener 302 combined with the inssert 314, as measured according to ASTM standard F543-07-Standard Specification and Test Methods for Metallic Bone Screws, is comparable to a solid screw having the same outer dimensions and constructed from the same material.

As illustrated in FIG. 9B, the expandable member 326 has been deployed with the biomaterial 100. The inssert 314 is then reintroduced into the lumen 310. The threads 316, 318 advance the distal end 328 of the inssert 314 into engagement with the neck portion 330 of the expandable member 326. The neck portion 330 is shown cut-away to illustrate the engagement with the threads 316. Locking screw 322 is engaged with the head 304 in order to secure the head 320 of the inssert 314 to the fastener 302.

In one embodiment, reinforcing fibers 334 extend between the expandable portion 326 and the neck portion 330. The reinforcing fibers 334 reduce elastic deformation of the fixation system 332 to create a more direct coupling with the fastener 302. The reinforcing fibers 334 can be the same or different material used to construct the neck portion 330 and the expandable member 326. The reinforcing fibers 334 are preferably substantially inelastic.

Figure 10:
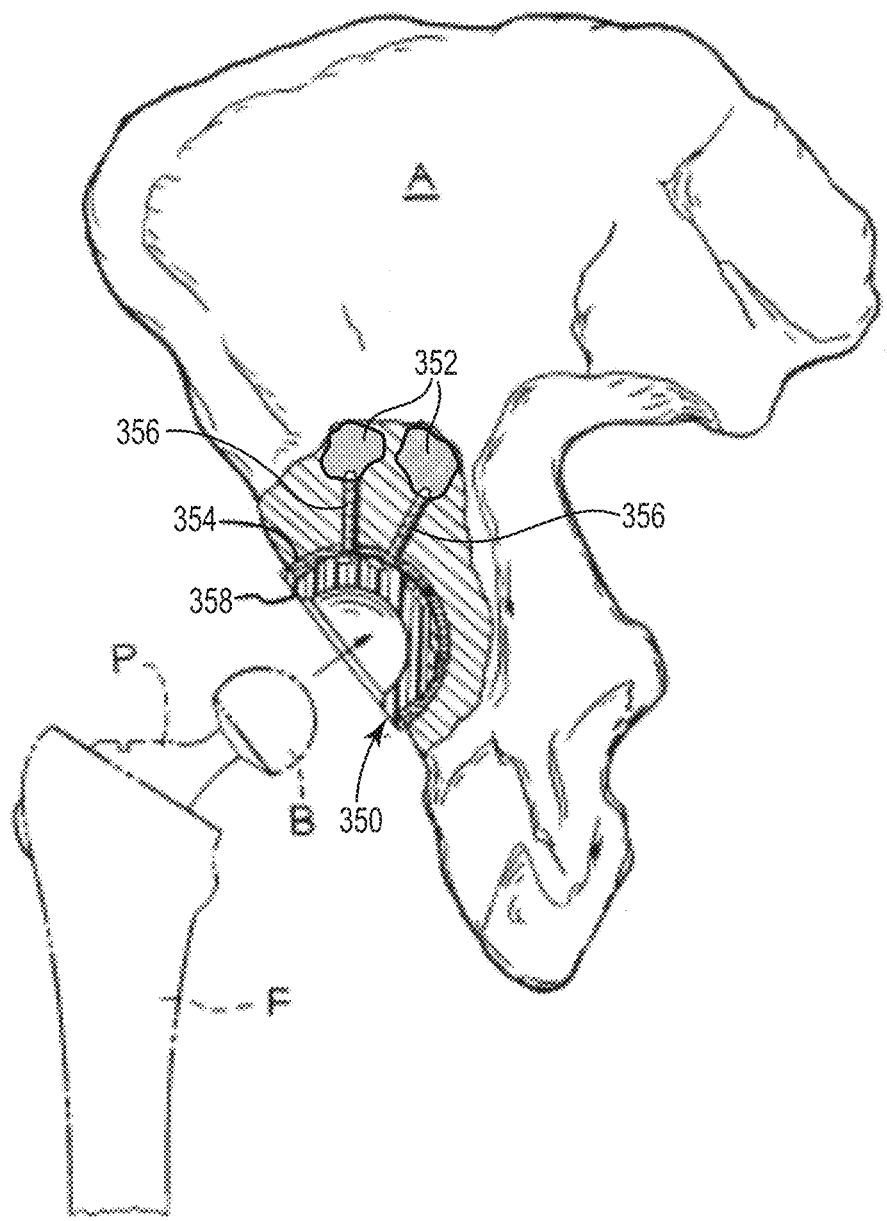
FIG. 10 illustrates an acetabular orthopedic implant with a fixation system in accordance with an embodiment of the present disclosure.

FIG. 10 illustrates acetabular cup assembly 350 secured using a fixation assemblies 352 in accordance with an embodiment of the present disclosure. Metal shell 354 of acetabular cup assembly 350 is implanted in acetabulum A using bone screws 356, as is known in the art. Acetabular cup member 358 is configured to receive a spherical ball B of a femoral hip joint prosthesis P which has been implanted in a femur F. An acetabular cup assembly suitable for use with the present fixation system is disclosed in U.S. Pat. No. 5,549,701 (Mikhail), which is hereby incorporated by reference. If the surgeon determines that the screws 356 are not sufficiently secure one or more of the present fixation assemblies 352 are added to the bone screws 356, as discussed above.

Figure 11:
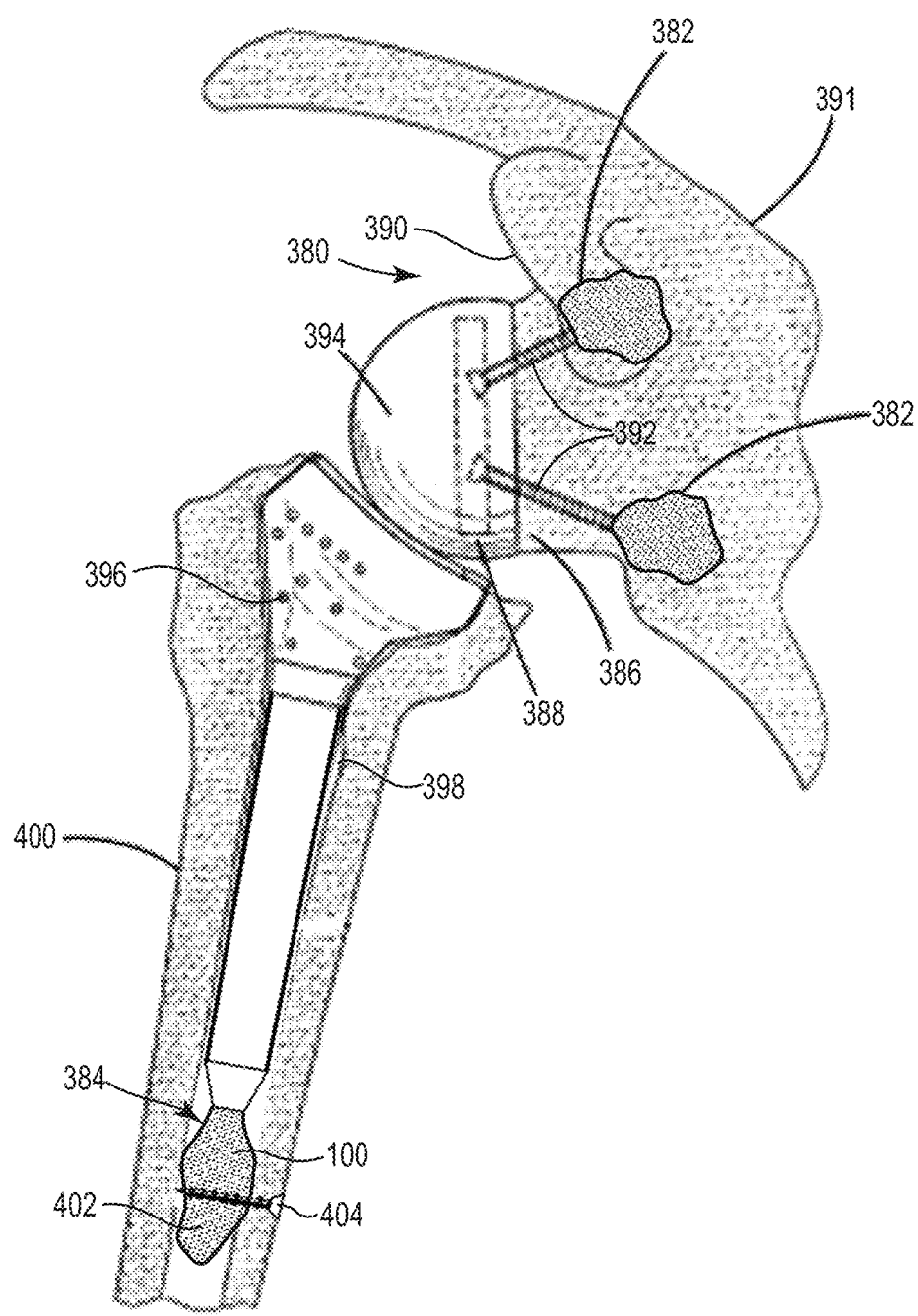
FIG. 11 illustrates a glenoidal orthopedic implant with a fixation system in accordance with an embodiment of the present disclosure.

FIG. 11 illustrates a total shoulder prosthesis 380 using a plurality of fixation assemblies 382, 384 in accordance with an embodiment of the present disclosure. Glenoid implant 386 includes plate 388 secured in the glenoid cavity 390 of the scapula 391 with a plurality of screws 392. The illustrated screws 392 each include fixation assemblies 382 such as discussed above. Glenoid sphere 394 is configured to be fitted over the plate 388. A shoulder prosthesis suitable for use with the present fixation assemblies 382, 384 is disclosed in U.S.

Patent Publication 2003/0114933 (Bouttens et al.), which is hereby incorporated by reference.

Humeral implant 396 is secured in medullar canal 398 of the humerus 400 using conventional techniques. Fixation system 384 extends into the medullar canal 398, where expandable member 402 is filled with biomaterial 100, as discussed herein. The humeral implant 396 includes a lumen with an insert that releasably secures the fixation system 384, as discussed herein. The fixation system 384 can be implanted using minimally invasive techniques, reducing damage to the bone 400.

Fastener 404, such as for example bone screws or pins, are optionally engaged with the expandable member 402. The porous nature of the expandable member 402 is self-healing so the biomaterial 100 does not flow out. The size of the expandable member 402 simplifies locating the fastener 404 relative to the humeral implant 396. The high tensile strength of the expandable member 402 serves to transfer loads on the humeral implant 396 across a greater surface area of the bone 84.

The present fixation system 384 can be used with any long bone, including the femur, tibia, and fibula, as well as arm bones including the radius, ulna, and humerus. The present expandable member 402 can be used with a variety of intramedullary devices, such as disclosed in U.S. Pat. No. 6,551,321 (Burkinshaw et al.); U.S. Pat. No. 3,779,239 (Fisher et al.); U.S. Pat. No. 5,053,035 (McLaren); U.S. Pat. No. 6,228,123 (Dezzani); U.S. Pat. No. 7,632,277 (Woll et al.); and U.S. Patent Publication Nos. 2006/0200142 (Sohngen et al.); 2006/0100623 (Pennig); 2010/0094292 (Parrott), which are hereby incorporated by reference.

FIGS. 12A-12B are schematic illustrations of a fixation system 420 with multiple expandable members 422A, 422B ("422") connected by neck portions 424A, 424B ("424") in accordance with an embodiment of the present disclosure. The fixation system 420 is optionally a unitary structure of woven fibers to provide high tensile strength along the length of the fixation system 420 or a modular structure (see FIG. 13). The present fixation system 420 can be used alone or in combination with another orthopedic implant.

In the illustrated embodiment, one or more check-valve assemblies 426A, 426B, 426C ("426") are optionally located in the fixation system 420 at various transition locations. The check-valve assemblies 426 can be secured to the fixation system 420 by a variety of techniques, such as adhesives, spot welding, compression rings, mechanical fasteners, and the like.

As illustrated in FIG. 12A, check-valve 426A is positioned to isolate expandable member 422A. The check-valve 426A permits the biomaterial 100 to be delivered through delivery tube 428 under pressure so as to displace any cancellous bone, without entering the other portions of the fixation system 420.

As illustrated in FIG. 12B, the delivery tube 428 is retracted in direction 430 and the check-valve 426A closes. Biomaterial is optionally delivered into neck portion 424A. Alternatively, since the neck portion 424A typically only operates in tension, no biomaterial is required. Distal end 432 of the delivery tube 428 next positioned in the expandable member 422B. Check-valves 426B, 426C isolate the biomaterial 100 in the expandable member 422B.

The delivery tube 428 is then removed and the neck portion 424B is secured to the orthopedic implant such as discussed herein.

FIG. 13 is an exploded view of a modular expandable member 450 for use in a fixation system in accordance with an embodiment of the present disclosure. Expandable member 452A, 452B ("452") include tubular couplings 454 with internal threads 456 and optional check-valves 458. The expandable members 452 can be bonded to the couplings 454 using a variety of techniques, such as adhesives, solvent bonding, mechanical deformation, mechanical interlock, spot welding, compression rings, or a variety of other techniques. In one embodiment, the expandable members 452 are a metal expandable member that is spot welded to metallic couplings 454.

Extension 460A, 460B ("460") similarly includes tubular couplings 462 with internal threads 464 similar to the internal threads 456. Hollow members 464 are provided with external threads 466 that mate with the internal threads 456, 464, permitting the expandable members 452 to be assembled in a modular fashion.

Figure 14:
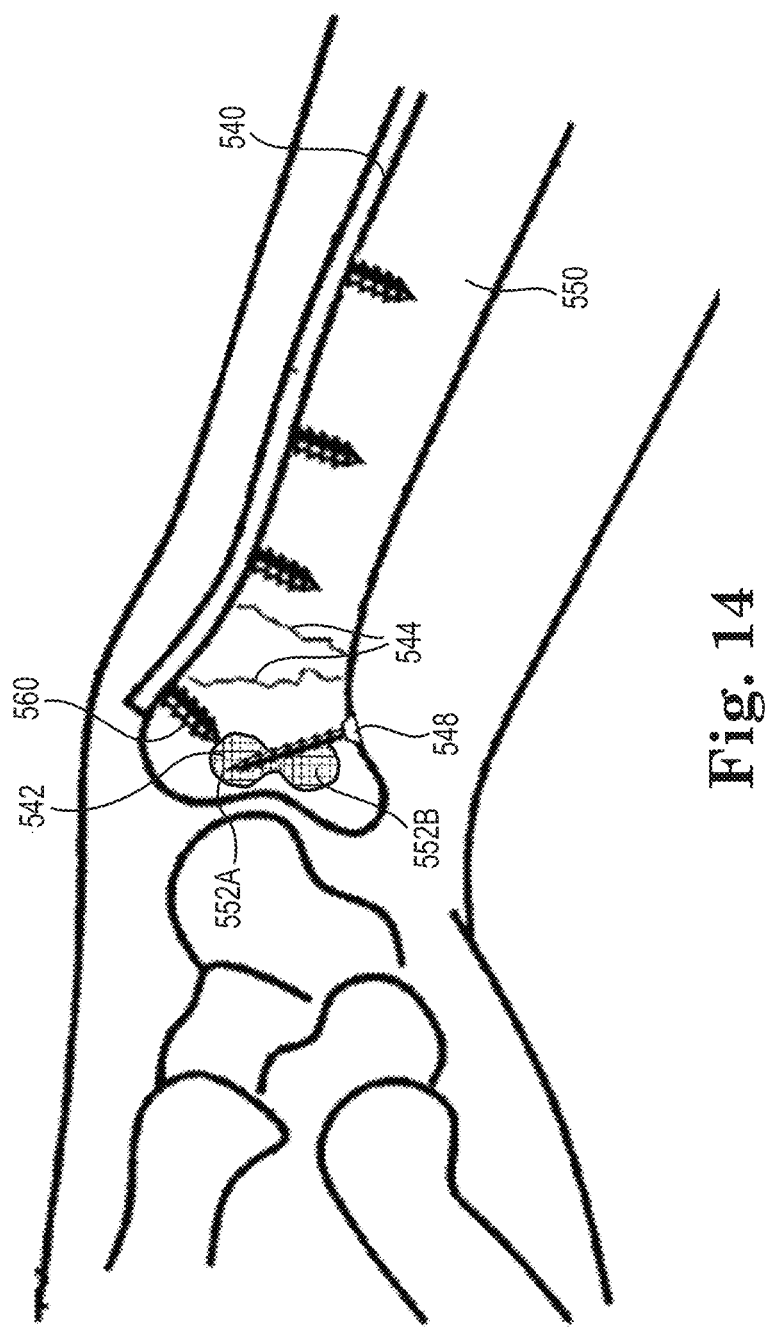
FIG. 14 illustrates a radial distal fraction plate with a fixation system in accordance with an embodiment of the present disclosure.

FIG. 14 illustrates bone plate 540 used in combination with bone screw 560 and fixation system 542 to reduce and secure distal radial fractures 544 in accordance with an embodiment of the present disclosure. The fixation system 542 includes multiple chambers 552A, 552B ("552"), such as illustrated in FIGS. 12 and 13. The embodiment of FIG. 14 is particularly useful where the cancellous bone is compromised and cannot adequately engage with fasteners 546. A bone plate and implantation methodology suitable for use with the present fixation system 542 is disclosed in U.S. Pat. No. 6,440,135 (Orbay et al.), which is hereby incorporated by reference.

In the illustrated embodiment, fastener 548 extends into the bone 550 from the opposite side and engages the expandable members 552 to provide bi-lateral fixation, without the need of complex mechanisms to align the fastener 548 with holes in the orthopedic implant 540. The expandable members 552 are relatively easy targets to hit due to their size. The pore size in the expandable members 552 is sufficiently small and the weave sufficiently tight that the fasteners 548 are securely engaged with the fixation system 542. The punctures of the expandable members 552 are preferably self-healing, so leakage of the biomaterial is minimized.

Figure 15:
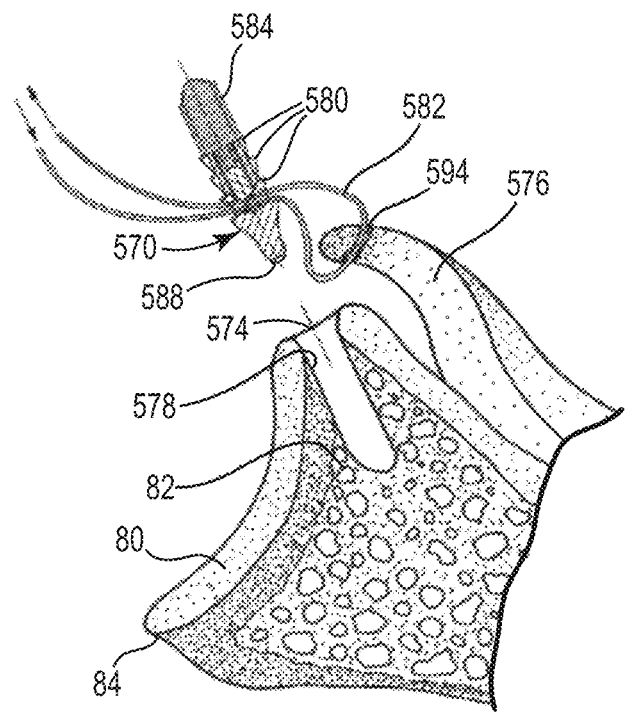
FIGS. 15 and 16 illustrate a bone anchor with a fixation system in accordance with an embodiment of the present disclosure.
Figure 16:
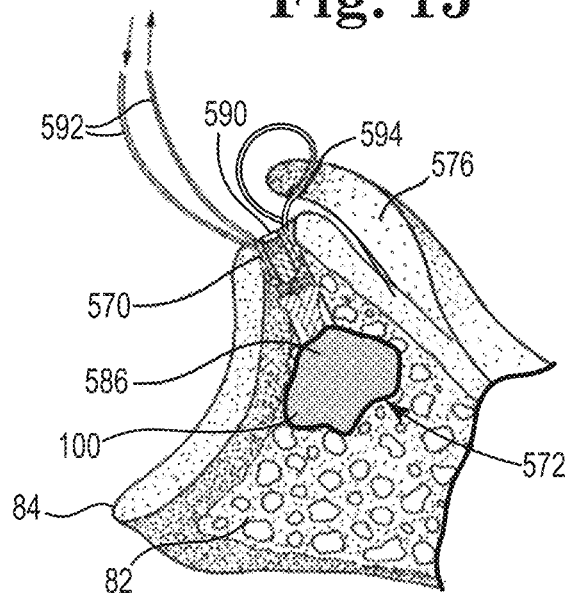

FIGS. 15 and 16 illustrate a knotless suture anchor 570 used with a fixation system 572 in accordance with an embodiment of the present disclosure. Bore 574 is formed in bone 84 in the area where tissue 576 is detached from the bone 84. The internal diameter 578 of the bore 574 is preferably slightly smaller than external diameter of projections 580 on the suture anchor 570.

Suture material 582 is threaded through opening 594 in tissue 576 and suture anchor 570. A variety of mechanisms can be used to engage the suture material 582 with the suture anchor 570, such as disclosed in U.S. Patent Publication Nos. 2007/0203498 (Gerber), 2006/0100630 (West, Jr.) and U.S. Pat. No. 6,146,406 (Shluzas et al.); U.S. Past. No. 6,770,076 (Foerster); U.S. Pat. No. 5,505,735 (Li); and U.S. Pat. No. 5,571,104 (Li), which are hereby incorporated by reference. The suture anchor 570 is then driven into the bore 574 using driver device 584. Projections 580 mechanically couple with cortical bone 80.

For some applications, expandable member 586 is optionally inserted through lumen 588 in the suture anchor 570 until it is positioned in the cancellous bone 82, as discussed herein. Biomaterial 100 is delivered into the expandable member 586 as illustrated in FIG. 16. Proximal end 590 of the expandable member 586 is then secured to the suture anchor 570 using a releasable fastener. Distal ends 592 of the suture material 582 are then tensioned by the surgeon as needed to attach the tissue 576 to the bone 84.

Figure 17A:
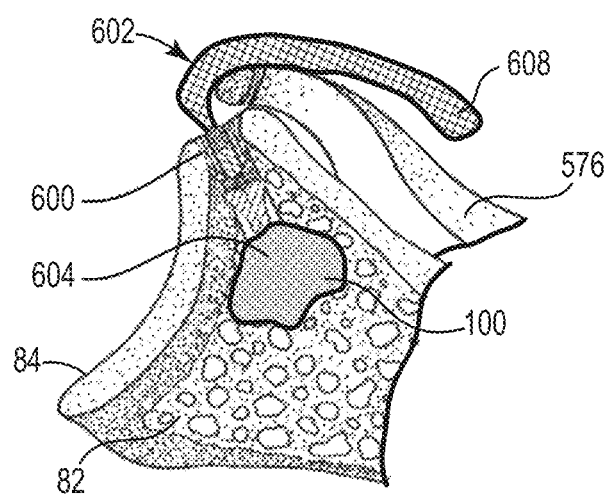
FIGS. 17A and 17B illustrate an alternate bone anchor with a fixation system in accordance with an embodiment of the present disclosure.
Figure 17B:
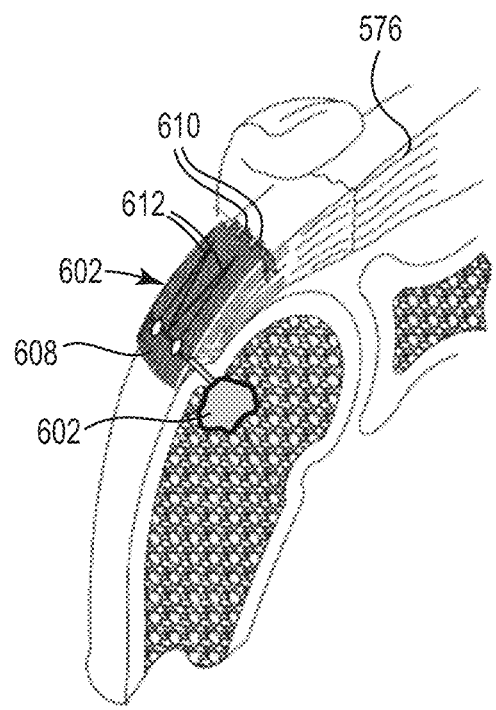

FIGS. 17A and 17B illustrate an alternate anchor 600 in which the fixation system 602 is attached directly to the tissue 576 in accordance with an embodiment of the present disclosure. The anchor 600 is implanted in the bone 84 and portion 604 of the expandable member 606 located in the cancellous bone 82 is filled with biomaterial 100 as discussed above. A check-valve structure such as illustrated in FIG. 10A is preferably located in the anchor 600 to retain the biomaterial 100 in the portion 604.

Portion 608 of the expandable member 606 extends beyond the anchor 600. In one embodiment, the portions 604 and 608 are a unitary, woven, porous structure. In another embodiment, the portion 608 is treated with a scaffolding for biological in-growth of the tissue 576, such as disclosed in U.S. Patent Publication Nos. 2010/0179591 (Saltzman et al.) or 2010/0298937 (Laurencin et al.), which are hereby incorporated by reference.

As illustrated in FIG. 17B, the portion 608 of the expandable member 606 is then secured to the tissue 576 using a variety of fasteners 610, such as sutures, staples, and the like, such as disclosed in U.S. Patent Publication No. 2010/0312275 (Euteneuer et al.), which is hereby incorporated by reference. Various tissue fastening structures can also be used to secure the tissue 576 to the portion 608, such as disclosed in U.S. Pat. No. 7,172,615 (Morriss), which is hereby incorporated by reference. Suture material 612 is optionally threaded through the portion 608 and placed under tension to apply tension to the tissue 576 relative to the fixation system 602.

FIGS. 18A and 18B illustrate a tissue fastening structure 620 used with fixation system 622 to secure tissue 624 to bone 84 in accordance with an embodiment of the present disclosure. Tissue fastening structure 620 includes post 626 that is inserted in bore 628 in cortical bone 80. Tab 630 preferably engaged with cortical bone 80 to secure the fastening structure 620. Fixation system 622 and biomaterial 100 are deployed into cancellous bone 82 through port 632. Fastener 634 releasably attaches fixation system 622 to the fastening structure 620, to permit future removal or revision.

In the illustrated embodiment, the tissue fastening structure 620 includes barbs 636 angled opposite tension direction 638 of tissue 624. The surgeon pulls the tissue 624 in direction 640 and engages the barbs 636.

FIG. 19 illustrates an alternate tissue fastening structure 650 with fixation system 652 in accordance with an embodiment of the present disclosure. Tissue fastening structure 650 includes barbs 654 configured to engage with tissue 656 as discussed above. In the illustrated embodiment, tissue fastening structure 650 is slidingly engaged with elongated ratcheting member 658 in order to adjust tension on tissue 656.

Proximal end 660 of the elongated ratcheting member 658 is secured to bone 84 by fixation system 652. In the illustrated embodiment, expandable member 662 and biomaterial 100 are delivered through portal 664 at proximal end 660.

FIG. 20A illustrates an alternate method using the kit 150 of FIG. 3 in accordance with an embodiment of the present disclosure. Distal end 198 of the sleeve 196 is inserted into the neck portion 162. In one embodiment, the neck portion 162 is temporarily attached to the sleeve 196, such as by a low-tack adhesive.

As illustrated in FIG. 20B, the delivery tube 174 is inserted through the sleeve 196 and into the expandable member 160, as discussed herein. In the preferred embodiment, the delivery tube 174, sleeve 196, and expandable member 160 are preassembled in the kit 150.

The delivery tube 174 is removed from the orthopedic implant 152 after delivery of the biomaterial 100, as illustrated in FIG. 20C. The insert 170 is positioned in the lumen 197 of the sleeve 196. The sleeve 196 guides the tip 168 into engagement with the neck portion 162. The sleeve 196 also protects the neck portion 162 from damage as the insert 170 is rotated into engagement with the orthopedic implant 152. In another embodiment, the sleeve 196 can be used to deliver the biomaterial 100 to the expandable member 160.

If the orthopedic implant 152 needs to be removed from the patient, the insert 170 is first removed. The sleeve 196 is removed from the patient along with the orthopedic implant 152. The act of unscrewing the orthopedic implant 152 from the bone will break any connection between the sleeve 196 and the neck portion 162.

FIGS. 21A-21C illustrate an orthopedic implant 700 configured for use with an optional fixation system 702 (see FIG. 8A) in accordance with an embodiment of the present disclosure. Neck portion 704 of the expandable member 706 extends generally the full length of the orthopedic implant 700. Delivery tube 708 is used to inflate the expandable member 706 and the neck portion 704 with biomaterial 100. In one embodiment, the delivery tube 708 is retracted during delivery of biomaterial 100 fills the entire lumen 710 is filled.

As illustrated in FIG. 21B, the biomaterial 100 substantially fills the lumen 710 of the orthopedic device 700. In the event that the biomaterial 100 does not bond to the orthopedic implant 700, threads 712 for the insert (see e.g., FIG. 1) mechanically interlock with the biomaterial 100 to secure the fixation device 702 to the orthopedic implant 700. In the illustrated embodiment, the biomaterial 100 acts as the insert.

In the illustrated embodiment, the expandable member 706 is tethered offset from distal end 714 of the orthopedic implant 700 by segment 716 of the neck portion 704. In an alternate embodiment, the expandable member 706 is in contact with the distal end 714 of the orthopedic device 700.

As illustrated in FIG. 21C, the orthopedic device 700 may be removed from the bone 84 by inserting a drill bit 718 into the lumen 710 and removing most of the biomaterial 100. The drill bit 718 preferably extends past the distal end 714 to sever the segment 716 of the neck portion 704 from the orthopedic implant 700. In this manner the biomaterial 100 and the expandable member 706 do not interfere with subsequent removal of the orthopedic implant 700. The orthopedic implant 700 is then unscrewed from the bone 84 using conventional techniques.

The expandable member 706 and the biomaterial 100 is abandoned in the bone 84. In embodiments where the biomaterial 100 is a bone growth material, the fixation system 702 will be substantially absorbed into the bone 84.

Figure 22:
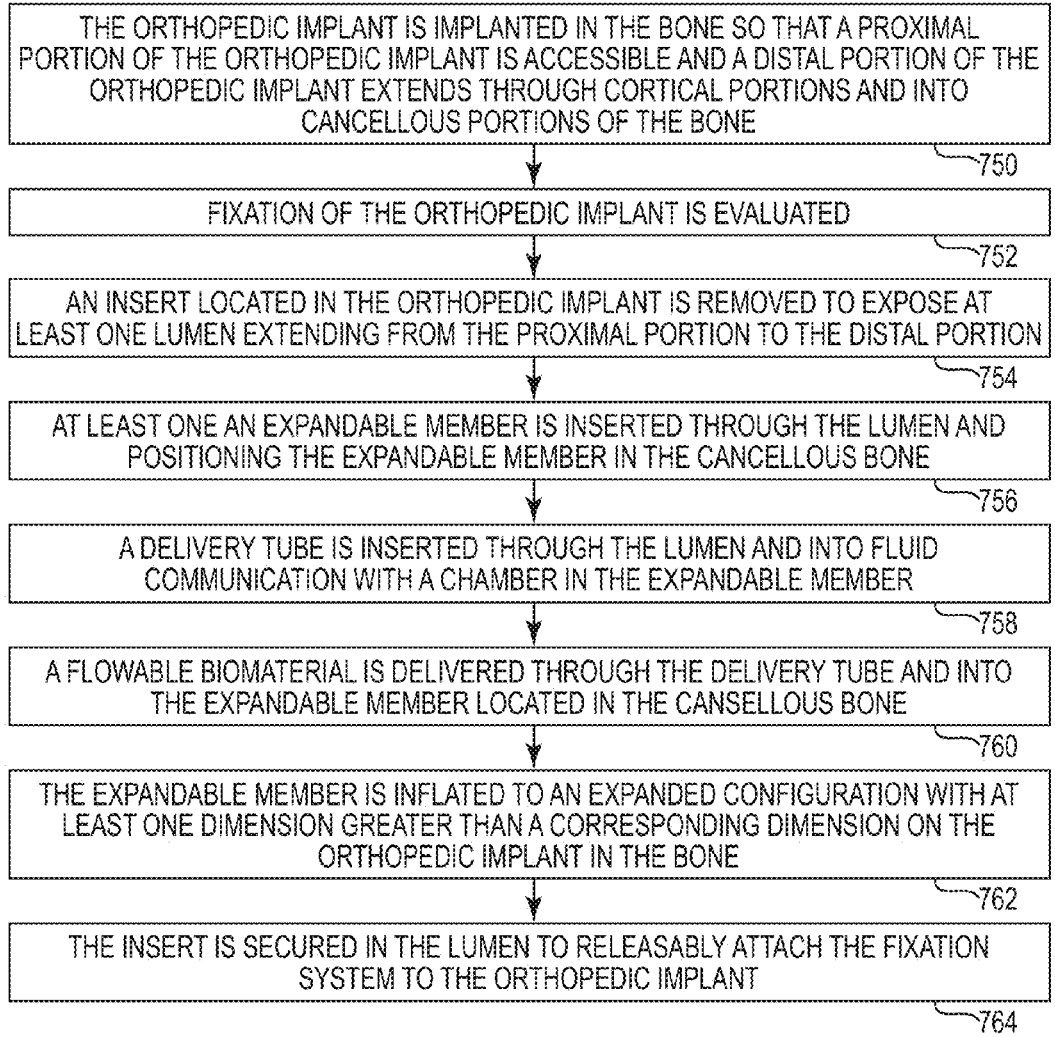
FIG. 22 is a flow chart of a method of implanting an orthopedic implant in a bone in accordance with an embodiment of the present disclosure.

FIG. 22 is a flow chart of a method of implanting an orthopedic implant in a bone in accordance with an embodiment of the present disclosure. The orthopedic implant is implanted in the bone so that a proximal portion of the orthopedic implant is accessible and a distal portion of the orthopedic implant extends through cortical portions and into cancellous portions of the bone (750). Fixation of the orthopedic implant is evaluated (752). An insert located in the orthopedic implant is removed to expose at least one lumen extending from the proximal portion to the distal portion (754). At least one expandable member is inserted through the lumen and positioning the expandable member in the cancellous bone (756). A delivery tube is inserted through the lumen and into fluid communication with a chamber in the expandable member (758). A flowable biomaterial is delivered through the delivery tube and into the expandable member located in the cancellous bone (760). The expandable member is inflated to an expanded configuration with at least one dimension greater than a corresponding dimension on the orthopedic implant in the bone (762). The insert is secured in the lumen to releasably attach the fixation system to the orthopedic implant (764).

FIG. 23A illustrates an alternate insert 800 for use with a fixation system 802 in accordance with an embodiment of the present disclosure. The expandable member 804 is implanted using the techniques disclosed herein, such as for example as shown in FIGS. 2F, 7C, 8B. Insert 800 includes a threaded tip 806 configured to extend through the lumen 808 and into the expandable member 804 and biomaterial 100. The threaded tip 806 can be used to supplement the attachment between the fastener 810 and the expandable member 804, or can be the sole attachment mechanism.

To remove the fastener 810 the insert 800 is removed. The fastener 810 is then removed from the bone 84 using conventional techniques. All that remains of the fixation system 802 is the biomaterial 100 and the expandable member 804.

Figure 24C:
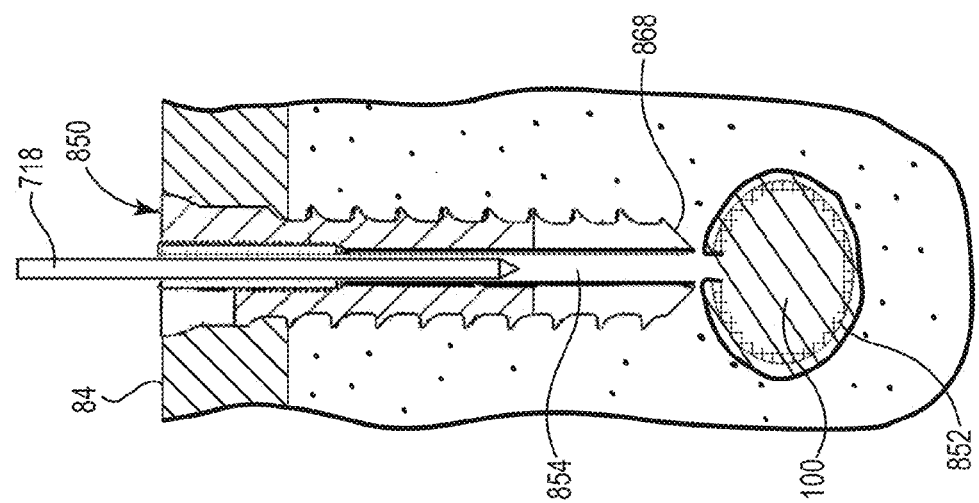
FIGS. 24A through 24C illustrate an alternate fixation structure for an orthopedic implant in accordance with an embodiment of the present disclosure.
Figure 24B:
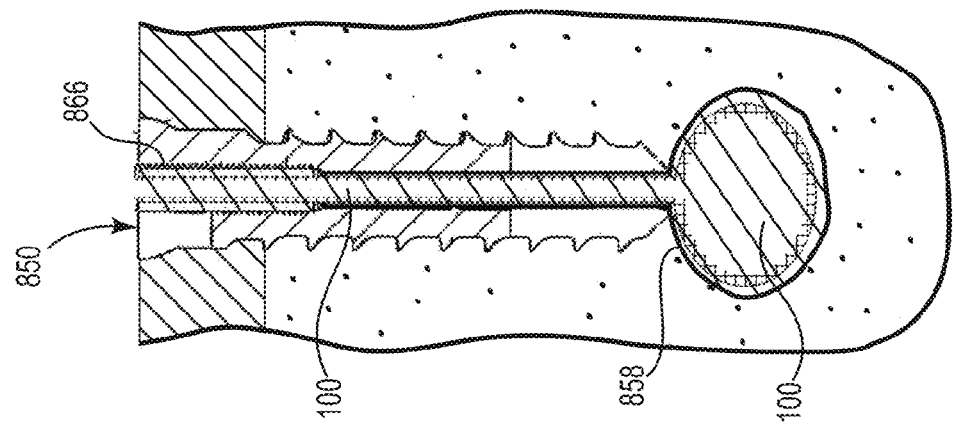
Figure 24A:
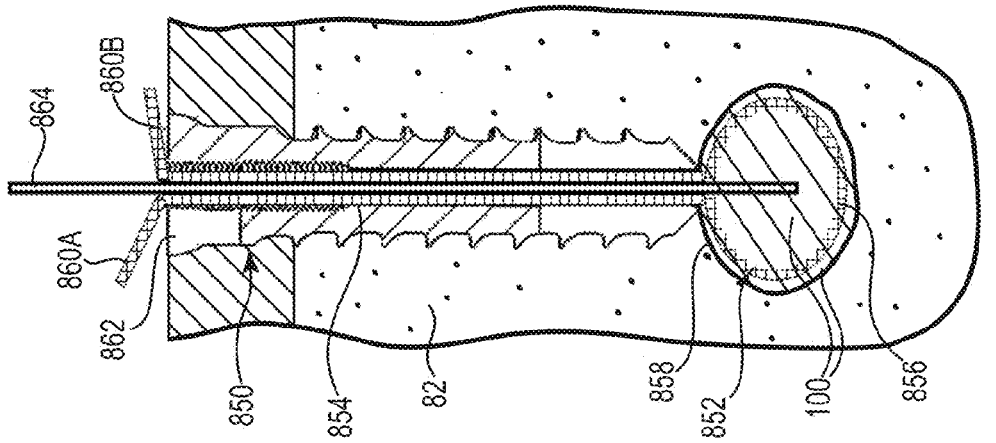

FIGS. 24A-24C illustrate an orthopedic implant 850 with one or more alternate fixation structures 852 in accordance with an embodiment of the present disclosure. The fixation structures 852 are elongated segments of biocompatible material positioned in lumen 854. The elongated segment can be configured as one or more filaments, ribbon shaped structure, a sling, a braided structure, and the like.

In one embodiment, the fixation structure 852 is a single segment of biocompatible material positioned in the lumen 854 so that center portions 856 is located in the cavity 858 in the cancellous bone 82. The fixation structure 852 can be made from any of the material disclosed herein, including mono-filaments, woven or non-woven materials, mesh, porous and non-porous sheet materials, suture material, and the like.

Proximal ends 860A, 860B of the fixation structures 852 are both preferably located outside the lumen 854 above the head 862. Delivery tube 864 is used to deliver the biomaterial 100 into the cavity 858. The biomaterial 100 secures the center portion 856 in the cavity 858. In one embodiment, the center portion 856 of the fixation structure 852 is embedded in the biomaterial 100.

As illustrated in FIG. 24B, the biomaterial 100 substantially fills the lumen 854 of the orthopedic device 850. In the event that the biomaterial 100 does not bond to the orthopedic implant 850, threads 866 for the insert (see e.g., FIG. 1) mechanically interlock with the biomaterial 100 to secure the fixation structure 852 to the orthopedic implant 850. In the illustrated embodiment, the biomaterial 100 acts as the insert. In another embodiment, the biomaterial 100 is located primarily in the cavity 858 and an insert such as illustrated in FIG. 1 is used to secure the fixation structure 852 to the orthopedic implant 850.

As illustrated in FIG. 24C, the orthopedic device 850 may be removed from the bone 84 by inserting a drill bit 718 into the lumen 854 and removing most of the biomaterial 100. The drill bit 718 preferably extends past the distal end 868 to sever the fixation structure 852 from the orthopedic implant 850. In this manner the biomaterial 100 and the fixation structure 852 do not interfere with subsequent removal of the orthopedic implant 850. The orthopedic implant 850 is then unscrewed from the bone 84 using conventional techniques.

The fixation structure 852 and the biomaterial 100 is abandoned in the bone 84. In embodiments where the biomaterial 100 is a bone growth material, the fixation structure 852 will be substantially absorbed into the bone 84.

FIG. 25 illustrates an orthopedic implant 880 with a plurality of alternate fixation structures 882 in accordance with an embodiment of the present disclosure. The fixation structures 882 are elongated segments of biocompatible material positioned in lumen 884.

In one embodiment, the fixation structure 882 is a rigid or semi-rigid polymer member with one or more barbs 886 positioned in the cavity 888 in the cancellous bone 82. The barbs 886 are designed to fold inward during insertion into the lumen 884, and hence, can have an expanded configuration larger than the lumen 884.

Proximal ends 890 of the fixation structures 882 preferably extend beyond the lumen 884 above the orthopedic implant 880. In one embodiment, a delivery tube (see e.g., FIG. 24A) is used to deliver the biomaterial 100 into the cavity 888. The barbs 886 are embedded in the biomaterial 100. In another embodiment, the lumen 884 is used to deliver the biomaterial 100 into the cavity 888. The biomaterial 100 can be delivered to the cavity 888 either before or after insertion of the fixation structures 882.

In one embodiment, an insert such as illustrated in FIG. 26A is used to secure the fixation structures 882 to the orthopedic implant 880. In another embodiment, the biomaterial 100 substantially fills the lumen 854 and secures the fixation structures 882.

FIGS. 26A and 26B illustrate an orthopedic implant 900 with an alternate fixation structures 902 in accordance with an embodiment of the present disclosure. The fixation structures 902 includes a proximal end 904 configured to engage with distal end 906 of the insert 908.

A variety of structures can be attached to, or molded onto, the proximate end 904. In the illustrated embodiment, one or more elongated members 910 are attached to the proximal end 904. In the preferred embodiment, the elongated members 910 are formed in a collapsed configuration 912 sized to fit in the lumen 914.

As inserted into the cavity 918 the distal ends 916 of the elongated members 910 engage with the cancellous bone 82 and are biased to expanded configuration 920 illustrated in FIG. 26B. The elongated members 910 are embedded in the biomaterial 100.

Example 1

Four identical fasteners were tested according ASTM standard F543-02 Annex A3 "Test Method for Determining the Axial Pullout Strength of Medical Bone Screws. The test was performed on a solid rigid polyurethane foam 40 millimeters×130 millimeters×180 millimeters block with a density of 20 pounds made according to Specification F1839, purchased from www.sawbones.com as product number 1522-03.

The fasteners had an outside diameter of about 9.0 millimeters with an outside threaded length of about 17 millimeters. The lumen had an inside diameter of about 6.0 millimeters.

Four pilot holes about 8.0 millimeters in diameter were drilled completely through the test block. A fastener was secured in each of the pilot holes. A cavity was formed behind the fasteners for Samples C and D using a wire with a bent tip attached to a cordless drill and inserted through the lumen of the fasteners. The drill was run at a moderate speed for about 20 seconds for each Sample.

Samples A and B were controls, without any fixation structure. Samples C and D included a fixation structure configured as an expandable member and constructed from a light gauze cotton mesh. The expandable members were inserted through the lumens and into cavities formed in the test block. Neck portions of the expandable members were located in the lumens of the fasteners.

The expandable members of Sample C was filled with a 30-minute epoxy resin and Sample D was filled with an expanding construction foam. Since the pilot holes extended through the entire thickness of the test block it was possible to view the delivery of the epoxy and form.

A 0.25-20 machine screws were threaded into the lumens of the control fasteners and the test fasteners to secure the neck portions of the expandable members to the fasteners. The heads of the machine screws were the attachment points for the pull-out test.

Table 1 below shows the results of the pull-out tests. The percent change is calculated relative to the average of control Samples A and B.

TABLE 1

| Sample | Description | Pull-out Force (Newtons) | Percent Change re: Average Control |
|---|---|---|---|
| A | Control | 1312 | Control |
| B | Control | 1342 | Control |
| C | Mesh Bag/Epoxy | 1798 | 35.5% increase |
| D | Mesh Bag/Expandable Foam | 1574 | 18.6% increase |

The failure mode for Samples A through D was for the test block to fracture around the screws.

Example 2

Four fasteners were tested according ASTM standard F543-02 Annex A3 "Test Method for Determining the Axial Pullout Strength of Medical Bone Screws, to evaluate a fixation structure having a ribbon shape.

The test was performed on a solid rigid polyurethane foam 40 millimeters×130 millimeters×180 millimeters block with a density of 20 pounds made according to Specification F1839, purchased from www.sawbones.com as product number 1522-03.

Pilot holes for Samples E and F had a diameter of about 6.3 millimeters and pilot holes for Samples G and H had a diameter of about 4.5 millimeters.

The fasteners for Samples E and F had an outside diameter of about 6.0 millimeters with an outside threaded length of about 11.0 millimeters. The lumen had an inside diameter of about 5.0 millimeters.

The fasteners for Samples G and H had an outside diameter of about 5.0 millimeters with an outside threaded length of about 9.0 millimeters. The lumen had an inside diameter of about 4.0 millimeters.

A cavity was formed behind the fasteners for Samples E and H using a bent wire attached to a cordless drill inserted through the lumen of the fasteners. The drill was run at a moderate speed for about 20 seconds.

Samples F and G were controls, without any fixation structure. Samples E and H included a fixation structure constructed from a ribbon light gauze cotton mesh. The fixation structures were inserted through the lumens so the center portions of the gauze ribbons were located in cavities formed in the test block. Distal ends of the gauze mesh extended out of the tops of the fasteners and were folded down against the surface of the test block. A 30-minute epoxy resin was injected through the lumens of the fasteners for Samples E and H.

Appropriate sized machine screws were threaded into the lumens of the fasteners. The machine screws secured the distal ends of the ribbon-shaped fixation structure to the fasteners in Samples E and H. The heads of the machine screws were the attachment points for the pull-out test.

Table 2 below shows the results of the pull-out tests. The percent increase in pull-out force for Sample E is measured relative to control Sample F. The percent increase in pull-out force for Sample H is measured relative to control Sample G.

TABLE 2

| Sample | Description | Pull-out Force (Newtons) | Percent Change re: Control Samples |
|---|---|---|---|
| E | Mesh Sling/Epoxy | 1278 | 93.3% increase |
| F | Control | 661 | Control |
| G | Control | 426 | Control |
| H | Mesh Sling/Epoxy | 932 | 118% increase |

Example 3

Three fasteners were tested according ASTM standard F543-02 Annex A3 "Test Method for Determining the Axial Pullout Strength of Medical Bone Screws, to evaluate a fixation structure having a ribbon shape.

The test was performed on a solid rigid polyurethane foam 40 millimeters×130 millimeters×180 millimeters block with a density of 20 pounds made according to Specification F1839, purchased from www.sawbones.com as product number 1522-03.

Pilot holes for Samples I, J, and K with a diameter of about 6.0 millimeters were drilled into the test block at a depth of about 2× the length of the fasteners, about 22 millimeters.

The fasteners for Samples I, J, and K had an outside diameter of about 6.0 millimeters with an outside threaded length of about 11.0 millimeters. The lumen had an inside diameter of about 5.0 millimeters.

A cavity was formed behind the fasteners for Samples J and K using a bent wire attached to a cordless drill inserted through the lumen of the fasteners. A generally cylindrical cavity was formed having a height of about 10 millimeters with a diameter of about 10 to about 12 millimeters.

Sample I was control, without any fixation structure.

Sample J included a fixation structure constructed from a ribbon light gauze cotton mesh. The fixation structures were inserted through the lumens so the center portions were located in cavities formed in the test block. Distal ends of the gauze mesh extended out of the tops of the fasteners and were folded down against the surface of the test block.

Sample K included a fixation structure was configured as an expandable member constructed from a light gauze cotton mesh. The expandable member was inserted through the lumen and located in cavity formed in the test block. The neck portion of the gauze mesh extended out of the tops of the fasteners.

For Samples J and K, a 30-minute epoxy resin was injected through the lumens of the fasteners and into the cavity.

Appropriate sized machine screws were threaded into the lumens of the fasteners. The machine screws secured the distal ends of the ribbon-shaped fixation structure to the fasteners in Samples I, J, and K. The heads of the machine screws were the attachment points for the pull-out test.

Table 3 below shows the results of the pull-out tests. The percent change in pull-out force for Samples J and K is calculated relative to control Sample I.

TABLE 3

| Sample | Description | Pull-out Force (Newtons) | Percent Change re: Control Sample |
|---|---|---|---|
| I | Control | 748 | Control |
| J | Mesh Sling/Epoxy | 1281 | 71.2% increase |
| K | Mesh Bag/Epoxy | 1050 | 40.3% increase |

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments of the disclosure. The upper and lower limits of these smaller ranges which may independently be included in the smaller ranges is also encompassed within the embodiments of the disclosure, subject to any specifically excluded limit in the stated range. Where the stated range includes one or both of the limits, ranges excluding either both of those included limits are also included in the embodiments of the present disclosure.

Unless defined otherwise, all technical and scientific terms used herein have the same meaning as commonly understood by one of ordinary skill in the art to which the embodiments of the present disclosure belong. Although any methods and materials similar or equivalent to those described herein can also be used in the practice or testing of the embodiments of the present disclosure, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments of the disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of the present disclosure. It should be understood that various features and aspects of the disclosed embodiments can be combined with or substituted for one another in order to form varying modes of the disclosed embodiments of the disclosure. Thus, it is intended that the scope of the present disclosure herein disclosed should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment(s) that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A fixation system that releasably secures to an orthopedic implant to supplement fixation of the orthopedic implant in a cancellous portion of a bone, the orthopedic implant having at least one lumen extending from a proximal portion to a distal portion configured to extend through cortical portions and into the cancellous portions of the bone, the fixation system that releasably secures to the orthopedic implant comprising:
   at least one expandable member configured to extend through the lumen of the orthopedic implant and into the cancellous bone near the distal portion of the orthopedic implant, the expandable member comprises at least one chamber;
   a flowable biomaterial that flows through the lumen and into the at least one chamber to inflate the expandable member to an expanded configuration located in the cancellous bone, the expanded configuration comprising at least one dimension greater than a corresponding dimension on the orthopedic implant located generally along a pull-out direction of the orthopedic implant; and
   an insert that releasably attaches the fixation system to the lumen of the orthopedic implant to supplement fixation of the orthopedic implant in the cancellous bone such that the expandable member is detachable from the orthopedic implant to facilitate subsequent removal of the orthopedic implant from the bone without removal of the biomaterial from the bone.

2. The fixation system of claim 1 wherein the expandable member comprises a porous structure with openings sized to permit intimate contact between the biomaterial and the cancellous bone.

3. The fixation system of claim 1 wherein the fixation system increases pull-out strength of the orthopedic implant along the pull-out direction by at least 40% as measured according to ASTM standard F543-02 Annex A3 relative to the orthopedic implant without the fixation system.

4. The fixation system of claim 1 wherein the expandable member in the expanded configuration includes at least one transverse dimension perpendicular to the pull-out direction that is at least 125% of a transverse dimension of a corresponding dimension on the orthopedic implant.

5. The fixation system of claim 1 wherein the expandable member includes a neck portion configured to be secured to the orthopedic implant by the insert.

6. The fixation system of claim 1 wherein the insert is configured to seal the lumen in the orthopedic implant when the fixation system is not employed.

7. The fixation system of claim 1 wherein the insert comprises a curable biomaterial located in the lumen.

8. The fixation system of claim 1 comprising a delivery tube configured to be inserted in the lumen and fluidly coupled to the expandable member to deliver a flowable biomaterial to the chamber.

9. The fixation system of claim 8 comprising at least one check-valve assembly on the expandable member configured to receive the delivery tube and to retain the flowable biomaterial in the chamber after the delivery tube is removed.

10. The fixation system of claim 8 comprising a biomaterial delivery system configured to fluidly couple with a proximal end of a delivery tube to delivery the biomaterial under pressure to the chamber in the expandable member.

11. The fixation system of claim 1 wherein the biomaterial comprises a resorbable, bone-growth stimulating composition that interacts with the cancellous bone through openings in the first expandable member.

12. The fixation system of claim 1 wherein the biomaterial is cured in-situ in contact with the cancellous bone near the distal portion of the orthopedic implant.

13. The fixation system of claim 1 comprising a plurality of discrete expandable members of different sizes and shapes.

14. A fixation system that releasably secures to an orthopedic implant to supplement fixation of the orthopedic implant in a cancellous portion of a bone, the orthopedic implant having at least: one lumen extending from a proximal portion to a distal portion configured to extend through cortical portions and into the cancellous portions of the bone, the fixation system that releasably secures to the orthopedic implant comprising:
- at least one expandable member configured to extend through the lumen in the orthopedic implant and into the cancellous portion of the bone past the distal portion of the orthopedic implant;
- a curable, flowable biomaterial that flows through the lumen into engagement with the fixation structure near the distal portion of the orthopedic implant and is configured to cure in-situ in contact with the cancellous bone, the expandable member and cured biomaterial located in the cancellous bone comprising at least one dimension greater than ac dimension on the orthopedic implant located generally along a pull-out direction of the orthopedic implant; and
- a securing structure that releasably secures the fixation system in the lumen of the orthopedic device to supplement fixation of the orthopedic implant in the cancellous bone, such that the expandable member is detachable from the orthopedic implant to facilitate subsequent removal of the orthopedic implant from the cancellous bone without removing the cured biomaterial from the bone.

15. A fixation system that releasably secures to an orthopedic implant to supplement fixation of the orthopedic implant in a cancellous portion era bone, the orthopedic implant having at least one lumen extending from a proximal portion to a distal portion configured to extend through cortical portions and into the cancellous portions of the bone, the fixation system that releasably secures to the orthopedic implant comprising:
- at least one fixation structure configured to extend through the lumen in the orthopedic implant and into the cancellous portion of the bone past the distal portion of the orthopedic implant;
- a curable, flowable biomaterial that flows through the lumen into engagement with the fixation structure near the distal portion of the orthopedic implant and is configured to cure in-situ in contact with the cancellous bone, the fixation structure and cured biomaterial located in the cancellous bone comprising at least one dimension greater than a corresponding dimension on the orthopedic implant located generally along pull-out direction of the orthopedic implant; and
- a curable biomaterial that cures in the lumen of the orthopedic implant to releasably attach the fixation system to the orthopedic implant to supplement fixation Of the orthopedic implant in the cancellous bone, such that the fixation structure is detachable from the orthopedic implant to facilitate subsequent removal of the orthopedic implant from the cancellous bone without removing the cured biomaterial from the bone.

16. The fixation system of claim 15 wherein the cured material cured in the lumen comprises the curable, flowable biomaterial.

17. The fixation system of claim 15 wherein the fixation structure comprises an expandable structure that is embedded in the cured biomaterial located in the cancellous bone.

18. The fixation system of claim 15 comprising a delivery tube inserted through the lumen to deliver the curable, flowable biomaterial into engagement with the fixation structure.

19. The fixation system of claim 15 wherein the curable, flowable biomaterial comprises a resorbable, bone-growth stimulating composition.

\* \* \* \* \*